United States Patent
Felföldi et al.

(10) Patent No.: US 9,416,164 B2
(45) Date of Patent: Aug. 16, 2016

(54) METHOD FOR THE PRODUCTION OF POLYPEPTIDES

(71) Applicant: Richter Gedeon Nyrt., Budapest (HU)

(72) Inventors: Ferenc Felföldi, Budapest (HU); Katalin Olasz, Budapest (HU); József Kozma, Budapest (HU)

(73) Assignee: Richter Gedeon Nyrt., Budapest (HU)

(*) Notice: Subject to any disclaimer, the term of this patent is extended or adjusted under 35 U.S.C. 154(b) by 17 days.

(21) Appl. No.: 14/386,081

(22) PCT Filed: Mar. 18, 2013

(86) PCT No.: PCT/EP2013/055529
§ 371 (c)(1),
(2) Date: Sep. 18, 2014

(87) PCT Pub. No.: WO2013/068602
PCT Pub. Date: May 16, 2013

(65) Prior Publication Data
US 2015/0044721 A1    Feb. 12, 2015

(30) Foreign Application Priority Data

Mar. 19, 2012 (HU) .................................. 1200171

(51) Int. Cl.
*C07K 14/535* (2006.01)
*C12P 21/02* (2006.01)

(52) U.S. Cl.
CPC ............... *C07K 14/535* (2013.01); *C12P 21/02* (2013.01)

(58) Field of Classification Search
None
See application file for complete search history.

(56) References Cited

U.S. PATENT DOCUMENTS

| | | | |
|---|---|---|---|
| 5,055,555 A | 10/1991 | Sassenfeld | |
| 5,681,720 A | 10/1997 | Kuga et al. | |
| 5,849,883 A | 12/1998 | Boone et al. | |
| 6,489,450 B2 | 12/2002 | Randolph et al. | |
| 2015/0057439 A1 | 2/2015 | Felföldi et al. | |

FOREIGN PATENT DOCUMENTS

| | | |
|---|---|---|
| CN | 101358196 A | 2/2009 |
| CN | 101691560 A | 4/2010 |
| EP | 0 219 874 A2 | 4/1987 |
| EP | 0 364 926 A2 | 4/1990 |
| EP | 0 237 545 B1 | 5/1991 |
| EP | 0 512 197 A1 | 11/1992 |
| EP | 1 630 173 A2 | 3/2006 |
| EP | 1 837 346 A2 | 9/2007 |
| WO | WO 87/01132 A1 | 2/1987 |
| WO | WO 89/10932 A1 | 11/1989 |
| WO | WO 98/53072 A1 | 11/1998 |
| WO | WO 00/02901 A1 | 1/2000 |
| WO | WO 01/04154 A1 | 1/2001 |
| WO | WO 01/87925 A1 | 11/2001 |
| WO | WO 03/051922 A1 | 6/2003 |
| WO | WO 04/001056 A1 | 12/2003 |
| WO | WO 2004/015124 A1 | 2/2004 |
| WO | WO 2006/097944 A2 | 9/2006 |
| WO | WO 2006/135176 A1 | 12/2006 |
| WO | WO 2008/096370 A2 | 8/2008 |
| WO | WO 2010/146599 A1 | 12/2010 |

OTHER PUBLICATIONS

Peternal et al. Microbial Cell Factories (2008) 7:34, 9 pages.*
Yan et al. Prot. Expres. Purif. (2006) 47, 645-650.*
Jevsevar et al. Biotechnol. Prog. (2005) 21, 632-639.*
International Search Report and Written Opinion for PCT/EP2013/055529 mailed Jun. 18, 2013.
International Preliminary Report on Patentability for PCT/EP2013/055529 mailed Oct. 2, 2014.
[No Author Listed], BL21(DE3) Competent Cells, BL21(DE3)pLysS Competent Cells, and BL21 Competent Cells. Instructional Manual, Revision B. Agilent Technologies. Created Jun. 9, 2011.
[No Author Listed], Filgrastim concentrated solution. European Pharmacopoeia. 7th ed. Jul. 15, 2011; Strasbourg: Council of Europe: 2015-18.
Baneyx et al., Recombinant protein folding and misfolding in *Escherichia coli*. Nat Biotechnol. Nov. 2004;22(11):1399-408.
Burgess, Purification of overproduced *Escherichia coli* RNA polymerase sigma factors by solubilizing inclusion bodies and refolding from Sarkosyl. Methods Enzymol. 1996;273:145-9.
Chen et al., Enhancement of the solubility of proteins overexpressed in *Escherichia coli* by heat shock. J Mol Microbiol Biotechnol. Nov. 2002;4(6):519-24.
Dale, Colony-stimulating factors for the management of neutropenia in cancer patients. Drugs. 2002;62 Suppl 1:1-15.
Devlin et al., Alteration of amino-terminal codons of human granulocyte-colony-stimulating factor increases expression levels and allows efficient processing by methionine aminopeptidase in *Escherichia coli*. Gene. May 15, 1988;65(1):13-22.
Dietrich et al., Industrial Protein Folding. Proteomics. BIOforum Europe. Darmstadt, Germany; Jan. 2003; 34-36.
Gelůnaite et al., Chelated mercury as a ligand in immobilized metal ion affinity chromatography of proteins. J Chromatogr A. Dec. 29, 2000;904(2):131-43.
Heidari et al., Expression, purification, and in vitro biological activities of recombinant bovine granulocyte-colony stimulating factor. Vet Immunol Immunopathol. Aug. 30, 2001;81(1-2):45-57.

(Continued)

*Primary Examiner* — Nashaat Nashed
(74) *Attorney, Agent, or Firm* — Wolf, Greenfield & Sacks, P.C.

(57) ABSTRACT

New methods for the production of recombinant polypeptides from inclusion bodies are disclosed. Modulation of the cell culture conditions positively affects the yield of the recombinant polypeptide in active form. In one aspect, the methods comprise (a) cultivating a host cell at a first temperature, the host cell comprising a nucleic acid encoding a recombinant polypeptide, (b) lowering the cultivation temperature from the first temperature to a second temperature, and (c) cultivating the host cell at the second temperature.

24 Claims, 4 Drawing Sheets

(56) References Cited

OTHER PUBLICATIONS

Holloway, Applications of recombinant DNA technology in the production of glycosylated recombinant human granulocyte colony stimulating factor. Eur J Cancer. 1994;30A Suppl 3:S2-6.

Kang et al., High level expression and simple purification of recombinant human granulocyte colony-stimulating factor in *E. coli*. Biotechnology Letters. Jul. 1995;17(7):687-92.

Khalilzadeh et al., Process development for production of human granulocyte-colony stimulating factor by high cell density cultivation of recombinant *Escherichia coli*. J Ind Microbiol Biotechnol. Dec. 2008;35(12):1643-50. doi: 10.1007/s10295-008-0408-8. Epub Aug. 6, 2008.

Lu et al., Folding and oxidation of recombinant human granulocyte colony stimulating factor produced in *Escherichia coli*. Characterization of the disulfide-reduced intermediates and cysteine—serine analogs. J Biol Chem. May 5, 1992;267(13):8770-7.

Marston, The purification of eukaryotic polypeptides synthesized in *Escherichia coli*. Biochem J. Nov. 15, 1986;240(1):1-12.

Martínez-Alonso et al., Learning about protein solubility from bacterial inclusion bodies. Microb Cell Fact. Jan. 8, 2009;8:4. doi: 10.1186/1475-2859-8-4.

Molineux, The design and development of pegfilgrastim (PEG-rmetHuG-CSF, Neulasta®). Curr Pharm Des. 2004;10(11):1235-44.

Ostervala, Purtification and renaturation of recombinant proteins produced in *Escherichia coli* as inclusion bodies. GE Healthcare. Application note 18-1112-33 AC. Apr. 2007:4 pages.

Peternel et al., New properties of inclusion bodies with implications for biotechnology. Biotechnol Appl Biochem. Apr. 2008;49(Pt 4):239-46.

Rao et al., A purification method for improving the process yield and quality of recombinant human granulocyte colony-stimulating factor expressed in *Escherichia coli* and its characterization. Biotechnol Appl Biochem. Jun. 2008;50(Pt 2):77-87.

Rudolph et al., In vitro folding of inclusion body proteins. FASEB J. Jan. 1996;10(1):49-56.

Rudolph, Renaturation of recombinant, disulfide-bonded proteins from "inclusion bodies" Modern Methods in Protein and Nucleic Acid Research (H. Tschesche, ed.). 1990, Walter de Gruyter, Berlin: 149-71.

Sørensen et al., Soluble expression of recombinant proteins in the cytoplasm of *Escherichia coli*. Microb Cell Fact. Jan. 4, 2005;4(1):1.

Vanz et al., Human granulocyte colony stimulating factor (hG-CSF): cloning, overexpression, purification and characterization. Microb Cell Fact. Apr. 4, 2008;7:13. doi:10.1186/1475-2859-7-13.

Wang et al., Refolding with simultaneous purification of recombinant human granulocyte colony-stimulating factor from *Escherichia coli* using strong anion exchange chromatography. Chinese Chemical Letters. 2005;16(3):389-92.

Welte et al., Filgrastim (r-metHuG-CSF): the first 10 years. Blood. Sep. 15, 1996;88(6):1907-29.

Wingfield et al., Characterization of recombinant-derived granulocyte-colony stimulating factor (G-CSF). Biochem J. Nov. 15, 1988;256(1):213-8.

Zsebo et al., Recombinant human granulocyte colony stimulating factor: molecular and biological characterization. Immunobiology. Sep. 1986;172(3-5):175-84.

\* cited by examiner

FIG. 1A

"G-CSF expression vector"

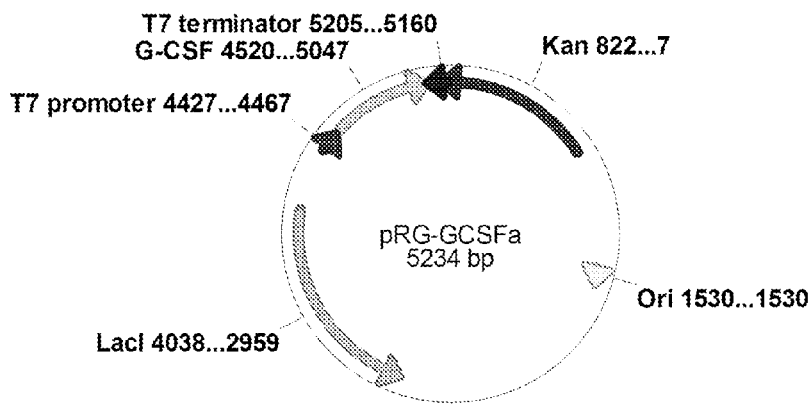

FIG. 1B

Seq.-ID 4: "Sequence of the G-CSF vector"
CAATTCTTAGAAAAACTCATCGAGCATCAAATGAAACTGCAATTTATTCATATCAGGATTATCAA
TACCATATTTTTGAAAAAGCCGTTTCTGTAATGAAGGAGAAAACTCACCGAGGCAGTTCCATAGG
ATGGCAAGATCCTGGTATCGGTCTGCGATTCCGACTCGTCCAACATCAATACAACCTATTAATTT
CCCCTCGTCAAAAATAAGGTTATCAAGTGAGAAATCACCATGAGTGACGACTGAATCCGGTGAGA
ATGGCAAAAGTTTATGCATTTCTTTCCAGACTTGTTCAACAGGCCAGCCATTACGCTCGTCATCA
AAATCACTCGCATCAACCAAACCGTTATTCATTCGTGATTGCGCCTGAGCGAGACGAAATACGCG
ATCGCTGTTAAAAGGACAATTACAAACAGGAATCGAATGCAACCGGCGCAGGAACACTGCCAGCG
CATCAACAATATTTTCACCTGAATCAGGATATTCTTCTAATACCTGGAATGCTGTTTTCCCGGGG
ATCGCAGTGGTGAGTAACCATGCATCATCAGGAGTACGGATAAAATGCTTGATGGTCGGAAGAGG
CATAAATTCCGTCAGCCAGTTTAGTCTGACCATCTCATCTGTAACATCATTGGCAACGCTACCTT
TGCCATGTTTCAGAAACAACTCTGGCGCATCGGGCTTCCCATACAATCGATAGATTGTCGCACCT
GATTGCCCGACATTATCGCGAGCCCATTTATACCCATATAAATCAGCATCCATGTTGGAATTTAA
TCGCGGCCTAGAGCAAGACGTTTCCCGTTGAATATGGCTCATAACACCCCTTGTATTACTGTTTA
TGTAAGCAGACAGTTTTATTGTTCATGACCAAAATCCCTTAACGTGAGTTTTCGTTCCACTGAGC
GTCAGACCCCGTAGAAAAGATCAAAGGATCTTCTTGAGATCCTTTTTTTCTGCGCGTAATCTGCT
GCTTGCAAACAAAAAAACCACCGCTACCAGCGGTGGTTTGTTTGCCGGATCAAGAGCTACCAACT
CTTTTTCCGAAGGTAACTGGCTTCAGCAGAGCGCAGATACCAAATACTGTCCTTCTAGTGTAGCC
GTAGTTAGGCCACCACTTCAAGAACTCTGTAGCACCGCCTACATACCTCGCTCTGCTAATCCTGT
TACCAGTGGCTGCTGCCAGTGGCGATAAGTCGTGTCTTACCGGGTTGGACTCAAGACGATAGTTA
CCGGATAAGGCGCAGCGGTCGGGCTGAACGGGGGGTTCGTGCACACAGCCCAGCTTGGAGCGAAC
GACCTACACCGAACTGAGATACCTACAGCGTGAGCTATGAGAAAGCGCCACGCTTCCCGAAGGGA
GAAAGGCGGACAGGTATCCGGTAAGCGGCAGGGTCGGAACAGGAGAGCGCACGAGGGAGCTTCCA
GGGGGAAACGCCTGGTATCTTTATAGTCCTGTCGGGTTTCGCCACCTCTGACTTGAGCGTCGATT
TTTGTGATGCTCGTCAGGGGGCGGAGCCTATGGAAAAACGCCAGCAACGCGGCCTTTTTACGGT

FIG. 1B (continued)

```
TCCTGGCCTTTTGCTGGCCTTTTGCTCACATGTTCTTTCCTGCGTTATCCCCTGATTCTGTGGAT
AACCGTATTACCGCCTTTGAGTGAGCTGATACCGCTCGCCGCAGCCGAACGACCGAGCGCAGCGA
GTCAGTGAGCGAGGAAGCGGAAGAGCGCCTGATGCGGTATTTTCTCCTTACGCATCTGTGCGGTA
TTTCACACCGCAATGGTGCACTCTCAGTACAATCTGCTCTGATGCCGCATAGTTAAGCCAGTATA
CACTCCGCTATCGCTACGTGACTGGGTCATGGCTGCGCCCCGACACCCGCCAACACCCGCTGACG
CGCCCTGACGGGCTTGTCTGCTCCCGGCATCCGCTTACAGACAAGCTGTGACCGTCTCCGGGAGC
TGCATGTGTCAGAGGTTTTCACCGTCATCACCGAAACGCGCGAGGCAGCTGCGGTAAAGCTCATC
AGCGTGGTCGTGAAGCGATTCACAGATGTCTGCCTGTTCATCCGCGTCCAGCTCGTTGAGTTTCT
CCAGAAGCGTTAATGTCTGGCTTCTGATAAAGCGGGCCATGTTAAGGGCGGTTTTTTCCTGTTTG
GTCACTGATGCCTCCGTGTAAGGGGGATTTCTGTTCATGGGGGTAATGATACCGATGAAACGAGA
GAGGATGCTCACGATACGGGTTACTGATGATGAACATGCCCGGTTACTGGAACGTTGTGAGGGTA
AACAACTGGCGGTATGGATGCGGCGGGACCAGAGAAAATCACTCAGGGTCAATGCCAGCGCTTC
GTTAATACAGATGTAGGTGTTCCACAGGGTAGCCAGCAGCATCCTGCGATGCAGATCCGGAACAT
AATGGTGCAGGGCGCTGACTTCCGCGTTTCCAGACTTTACGAAACACGGAAACCGAAGACCATTC
ATGTTGTTGCTCAGGTCGCAGACGTTTTGCAGCAGCAGTCGCTTCACGTTCGCTCGCGTATCGGT
GATTCATTCTGCTAACCAGTAAGGCAACCCCGCCAGCCTAGCCGGGTCCTCAACGACAGGAGCAC
GATCATGCGCACCCGTGGGCCGCCATGCCGGCGATAATGGCCTGCTTCTCGCCGAAACGTTTGG
TGGCGGGACCAGTGACGAAGGCTTGAGCGAGGGCGTGCAAGATTCCGAATACCGCAAGCGACAGG
CCGATCATCGTCGCGCTCCAGCGAAAGCGGTCCTCGCCGAAAATGACCCAGAGCGCTGCCGGCAC
CTGTCCTACGAGTTGCATGATAAAGAAGACAGTCATAAGTGCGGCGACGATAGTCATGCCCCGCG
CCCACCGGAAGGAGCTGACTGGGTTGAAGGCTCTCAAGGGCATCGGTCGAGATCCCGGTGCCTAA
TGAGTGAGCTAACTTACATTAATTGCGTTGCGCTCACTGCCCGCTTTCCAGTCGGGAAACCTGTC
GTGCCAGCTGCATTAATGAATCGGCCAACGCGCGGGAGAGGCGGTTTGCGTATTGGGCGCCAGG
GTGGTTTTTCTTTTCACCAGTGAGACGGGCAACAGCTGATTGCCCTTCACCGCCTGGCCCTGAGA
GAGTTGCAGCAAGCGGTCCACGCTGGTTTGCCCCAGCAGGCGAAAATCCTGTTTGATGGTGGTTA
ACGGCGGGATATAACATGAGCTGTCTTCGGTATCGTCGTATCCCACTACCGAGATGTCCGCACCA
ACGCGCAGCCCGGACTCGGTAATGGCGCGCATTGCGCCCAGCGCCATCTGATCGTTGGCAACCAG
CATCGCAGTGGGAACGATGCCCTCATTCAGCATTTGCATGGTTTGTTGAAAACCGGACATGGCAC
TCCAGTCGCCTTCCCGTTCCGCTATCGGCTGAATTTGATTGCGAGTGAGATATTTATGCCAGCCA
GCCAGACGCAGACGCGCCGAGACAGAACTTAATGGGCCCGCTAACAGCGCGATTTGCTGGTGACC
CAATGCGACCAGATGCTCCACGCCCAGTCGCGTACCGTCTTCATGGGAGAAAATAATACTGTTGA
TGGGTGTCTGGTCAGAGACATCAAGAAATAACGCCGGAACATTAGTGCAGGCAGCTTCCACAGCA
ATGGCATCCTGGTCATCCAGCGGATAGTTAATGATCAGCCCACTGACGCGTTGCGCGAGAAGATT
GTGCACCGCCGCTTTACAGGCTTCGACGCCGCTTCGTTCTACCATCGACACCACCACGCTGGCAC
CCAGTTGATCGGCGCGAGATTTAATCGCCGCGACAATTTGCGACGGCGCGTGCAGGGCCAGACTG
GAGGTGGCAACGCCAATCAGCAACGACTGTTTGCCCGCCAGTTGTTGTGCCACGCGGTTGGGAAT
GTAATTCAGCTCCGCCATCGCCGCTTCCACTTTTTCCCGCGTTTTCGCAGAAACGTGGCTGGCCT
GGTTCACCACGCGGGAAACGGTCTGATAAGAGACACCGGCATACTCTGCGACATCGTATAACGTT
ACTGGTTTCACATTCACCACCCTGAATTGACTCTCTTCCGGGCGCTATCATGCCATACCGCGAAA
GGTTTTGCGCCATTCGATGGTGTCCGGGATCTCGACGCTCTCCCTTATGCGACTCCTGCATTAGG
AAGCAGCCCAGTAGTAGGTTGAGGCCGTTGAGCACCGCCGCCGCAAGGAATGGTGCATGCAAGGA
GATGGCGCCCAACAGTCCCCCGGCCACGGGGCCTGCCACCATACCCACGCCGAAACAAGCGCTCA
TGAGCCCGAAGTGGCGAGCCCGATCTTCCCCATCGGTGATGTCGGCGATATAGGCGCCAGCAACC
GCACCTGTGGCGCCGGTGATGCCGGCCACGATGCGTCCGGCGTAGAGGATCGAGATCGATCTCGA
TCCCGCGAAATTAATACGACTCACTATAGGGAATTGTGAGCGGATAACAATTCCCCTCTAGAAA
TAATTTTGTTTAACTTTAAGAAGGAGATATACATATGACTCCATTAGGTCCTGCTTCTTCTCTGC
CGCAAAGCTTTCTGCTGAAATGTCTGGAACAGGTTCGTAAAATCCAGGGTGACGGTGCTGCACTG
CAAGAAAAACTGTGCGCTACTTACAAACTGTGCCATCCGGAAGAGCTGGTACTGCTGGGTCATTC
TCTTGGGATCCCGTGGGCTCCGCTGTCTTCTTGTCCATCTCAAGCTCTTCAGCTGGCTGGTTGTC
TGTCTCAACTGCATTCTGGTCTGTTCCTGTATCAGGGTCTTCTGCAAGCTCTGGAAGGTATCTCT
CCGGAACTGGGTCCGACTCTGGACACTCTGCAGCTAGATGTAGCTGACTTTGCTACTACTATTTG
```

FIG. 1B (continued)

```
GCAACAGATGGAAGAGCTCGGTATGGCACCAGCTCTGCAACCGACTCAAGGTGCTATGCCGGCAT
TCGCTTCTGCATTCCAGCGTCGTGCAGGAGGTGTACTGGTTGCTTCTCATCTGCAATCTTTCCTG
GAAGTATCTTACCGTGTTCTGCGTCATCTGGCTCAGCCGTAATAAGCTCGAGCACCACCACCACC
ACCACCACCACTAATTGATTAATACCTAGGCTGCTAAACAAAGCCCGAAAGGAAGCTGAGTTGGC
TGCTGCCACCGCTGAGCAATAACTAGCATAACCCCTTGGGGCCTCTAAACGGGTCTTGAGGGGTT
TTTTGCTGAAAGGAGGAACTATATCCGGATCTAG
```

FIG. 2: Comparison of SEC-HPLC chromatograms from a purity analysis of a commercially available filgrastim drug product (3A) used as reference and the product purified according the present invention (3B). Details are described in the examples.
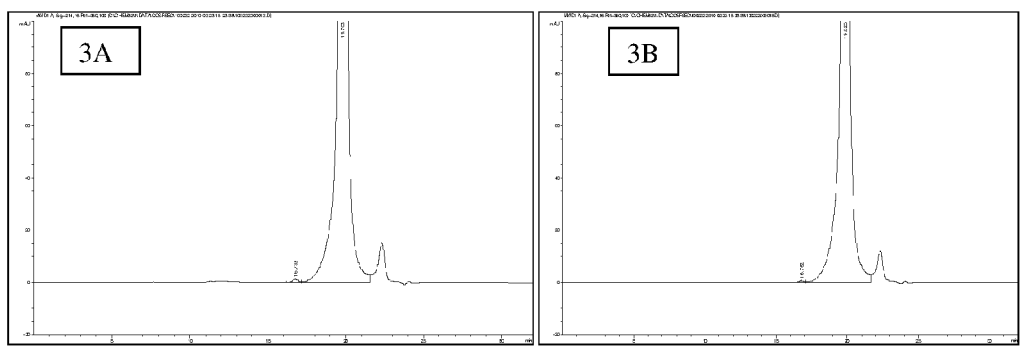

SEQUENCE LISTING

```
<160> NUMBER OF SEQ ID NOS: 6

<210> SEQ ID NO 1
<211> LENGTH: 174
<212> TYPE: PRT
<213> ORGANISM: Homo sapiens

<400> SEQUENCE: 1

Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
```

```
                     20                  25                  30
Glu Lys Leu Cys Ala Thr Tyr Lys Leu Cys His Pro Glu Glu Leu Val
             35                  40                  45

Leu Leu Gly His Ser Leu Gly Ile Pro Trp Ala Pro Leu Ser Ser Cys
     50                  55                  60

Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
            115                 120                 125

Ala Leu Gln Pro Thr Gln Gly Ala Met Pro Ala Phe Ala Ser Ala Phe
        130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170

<210> SEQ ID NO 2
<211> LENGTH: 174
<212> TYPE: PRT
<213> ORGANISM: Bos taurus

<400> SEQUENCE: 2

Thr Pro Leu Gly Pro Ala Arg Ser Leu Pro Gln Ser Phe Leu Leu Lys
  1               5                  10                  15

Cys Leu Glu Gln Val Arg Lys Ile Gln Ala Asp Gly Ala Glu Leu Gln
             20                  25                  30

Glu Arg Leu Cys Ala Ala His Lys Leu Cys His Pro Glu Glu Leu Met
             35                  40                  45

Leu Leu Arg His Ser Leu Gly Ile Pro Gln Ala Pro Leu Ser Ser Cys
     50                  55                  60

Ser Ser Gln Ser Leu Gln Leu Arg Gly Cys Leu Asn Gln Leu His Gly
 65                  70                  75                  80

Gly Leu Phe Leu Tyr Gln Gly Leu Leu Gln Ala Leu Ala Gly Ile Ser
                 85                  90                  95

Pro Glu Leu Ala Pro Thr Leu Asp Thr Leu Gln Leu Asp Val Thr Asp
            100                 105                 110

Phe Ala Thr Asn Ile Trp Leu Gln Met Glu Asp Leu Gly Ala Ala Pro
            115                 120                 125

Ala Val Gln Pro Thr Gln Gly Ala Met Pro Thr Phe Thr Ser Ala Phe
        130                 135                 140

Gln Arg Arg Ala Gly Gly Val Leu Val Ala Ser Gln Leu His Arg Phe
145                 150                 155                 160

Leu Glu Leu Ala Tyr Arg Gly Leu Arg Tyr Leu Ala Glu Pro
                165                 170

<210> SEQ ID NO 3
<211> LENGTH: 175
<212> TYPE: PRT
<213> ORGANISM: Homo sapiens

<400> SEQUENCE: 3

Met Thr Pro Leu Gly Pro Ala Ser Ser Leu Pro Gln Ser Phe Leu Leu
```

```
1               5                  10                 15
Lys Cys Leu Glu Gln Val Arg Lys Ile Gln Gly Asp Gly Ala Ala Leu
                    20                  25                  30

Gln Glu Lys Leu Cys Ala Thr Tyr Lys Leu Cys His Pro Glu Glu Leu
                35                  40                  45

Val Leu Leu Gly His Ser Leu Gly Ile Pro Trp Ala Pro Leu Ser Ser
            50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                    85                  90                  95

Ser Pro Glu Leu Gly Pro Thr Leu Asp Thr Leu Gln Leu Asp Val Ala
                100                 105                 110

Asp Phe Ala Thr Thr Ile Trp Gln Gln Met Glu Glu Leu Gly Met Ala
                115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                    165                 170                 175
```

<210> SEQ ID NO 4
<211> LENGTH: 5234
<212> TYPE: DNA
<213> ORGANISM: Artificial Sequence
<220> FEATURE:
<223> OTHER INFORMATION: Sequence of the G-CSF vector

<400> SEQUENCE: 4

```
caattcttag aaaaactcat cgagcatcaa atgaaactgc aatttattca tatcaggatt      60
atcaatacca tatttttgaa aaagccgttt ctgtaatgaa ggagaaaact caccgaggca     120
gttccatagg atggcaagat cctggtatcg gtctgcgatt ccgactcgtc aacatcaat     180
acaacctatt aatttcccct cgtcaaaaat aaggttatca agtgagaaat caccatgagt     240
gacgactgaa tccggtgaga atggcaaaag tttatgcatt tctttccaga cttgttcaac     300
aggccagcca ttacgctcgt catcaaaatc actcgcatca accaaaccgt tattcattcg     360
tgattgcgcc tgagcgagac gaaatacgcg atcgctgtta aaaggacaat acaaacagg      420
aatcgaatgc aaccggcgca ggaacactgc cagcgcatca acaatatttt cacctgaatc     480
aggatattct tctaatacct ggaatgctgt ttttcccgggg atcgcagtgg tgagtaacca     540
tgcatcatca ggagtacgga taaaatgctt gatggtcgga agaggcataa attccgtcag     600
ccagtttagt ctgaccatct catctgtaac atcattggca acgctacctt tgccatgttt     660
cagaaacaac tctggcgcat cgggcttccc atacaatcga tagattgtcg cacctgattg     720
cccgacatta tcgcgagccc atttataccc atataaatca gcatccatgt tggaatttaa     780
tcgcggccta gagcaagacg tttcccgttg aatatggctc ataacacccc ttgtattact     840
gtttatgtaa gcagacagtt ttattgttca tgaccaaaat cccttaacgt gagttttcgt     900
tccactgagc gtcagacccc gtagaaaaga tcaaggatc ttcttgagat ccttttttc      960
tgcgcgtaat ctgctgcttg caacaaaaaa accaccgct accagcggtg gtttgtttgc    1020
cggatcaaga gctaccaact cttttttccga aggtaactgg cttcagcaga gcgcagatac    1080
caaatactgt ccttctagtg tagccgtagt taggccacca cttcaagaac tctgtagcac    1140
```

```
cgcctacata cctcgctctg ctaatcctgt taccagtggc tgctgccagt ggcgataagt    1200
cgtgtcttac cgggttggac tcaagacgat agttaccgga taaggcgcag cggtcgggct    1260 gaacggggg ttcgtgcaca cagcccagct tggagcgaac gacctacacc gaactgagat    1320
acctacagcg tgagctatga gaaagcgcca cgcttcccga agggagaaag gcggacaggt    1380
atccggtaag cggcagggtc ggaacaggag agcgcacgag ggagcttcca ggggaaacg    1440 cctggtatct ttatagtcct gtcgggtttc gccacctctg acttgagcgt cgattttgt    1500 gatgctcgtc aggggggcgg agcctatgga aaaacgccag caacgcggcc ttttacggt    1560 tcctggcctt ttgctggcct tttgctcaca tgttctttcc tgcgttatcc cctgattctg    1620
tggataaccg tattaccgcc tttgagtgag ctgataccgc tcgccgcagc cgaacgaccg    1680
agcgcagcga gtcagtgagc gaggaagcgg aagagcgcct gatgcggtat tttctcctta    1740
cgcatctgtg cggtatttca caccgcaatg gtgcactctc agtacaatct gctctgatgc    1800
cgcatagtta agccagtata cactccgcta tcgctacgtg actgggtcat ggctgcgccc    1860
cgacacccgc caacacccgc tgacgcgccc tgacgggctt gtctgctccc ggcatccgct    1920
tacagacaag ctgtgaccgt ctccgggagc tgcatgtgtc agaggttttc accgtcatca    1980
ccgaaacgcg cgaggcagct gcggtaaagc tcatcagcgt ggtcgtgaag cgattcacag    2040
atgtctgcct gttcatccgc gtccagctcg ttgagtttct ccagaagcgt taatgtctgg    2100
cttctgataa agcgggccat gttaagggcg ttttttcct gtttggtcac tgatgcctcc    2160
gtgtaagggg gatttctgtt catgggggta atgataccga tgaaacgaga gaggatgctc    2220
acgatacggg ttactgatga tgaacatgcc cggttactgg aacgttgtga gggtaaacaa    2280
ctggcggtat ggatgcggcg ggaccagaga aaaatcactc agggtcaatg ccagcgcttc    2340
gttaatacag atgtaggtgt tccacagggt agccagcagc atcctgcgat gcagatccgg    2400
aacataatgg tgcagggcgc tgacttccgc gtttccagac tttacgaaac acggaaaccg    2460
aagaccattc atgttgttgc tcaggtcgca gacgttttgc agcagcagtc gcttcacgtt    2520
cgctcgcgta tcggtgattc attctgctaa ccagtaaggc aaccccgcca gcctagccgg    2580
gtcctcaacg acaggagcac gatcatgcgc acccgtgggg ccgccatgcc ggcgataatg    2640
gcctgcttct cgccgaaacg tttggtggcg ggaccagtga cgaaggcttg agcgagggcg    2700
tgcaagattc cgaataccgc aagcgacagg ccgatcatcg tcgcgctcca gcgaaagcgg    2760
tcctcgccga aaatgaccca gagcgctgcc ggcacctgtc ctacgagttg catgataaag    2820
aagacagtca taagtgcggc gacgatagtc atgccccgcg cccaccggaa ggagctgact    2880
gggttgaagg ctctcaaggg catcggtcga gatcccggtg cctaatgagt gagctaactt    2940
acattaattg cgttgcgctc actgcccgct ttccagtcgg gaaacctgtc gtgccagctg    3000
cattaatgaa tcggccaacg cgcgggaga ggcggtttgc gtattgggcg ccagggtggt    3060
ttttcttttc accagtgaga cgggcaacag ctgattgccc ttcaccgcct ggccctgaga    3120
gagttgcagc aagcggtcca cgctggtttg ccccagcagg cgaaaatcct gtttgatggt    3180
ggttaacggc gggatataac atgagctgtc ttcggtatcg tcgtatccca ctaccgagat    3240
gtccgcacca acgcgcagcc cggactcggt aatggcgcgc attgcgccca cgccatctg    3300 atcgttggca accagcatcg cagtgggaac gatgccctca ttcagcattt gcatggtttg    3360
ttgaaaaccg gacatggcac tccagtcgcc ttccgttcc gctatcggct gaatttgatt    3420
gcgagtgaga tatttatgcc agccagccag acgcagacgc gccgagacag aacttaatgg    3480
```

```
gcccgctaac agcgcgattt gctggtgacc caatgcgacc agatgctcca cgcccagtcg   3540
cgtaccgtct tcatgggaga aaataatact gttgatgggt gtctggtcag agacatcaag   3600
aaataacgcc ggaacattag tgcaggcagc ttccacagca atggcatcct ggtcatccag   3660
cggatagtta atgatcagcc cactgacgcg ttgcgcgaga agattgtgca ccgccgcttt   3720
acaggcttcg acgccgcttc gttctaccat cgacaccacc acgctggcac ccagttgatc   3780
ggcgcgagat ttaatcgccg cgacaatttg cgacggcgcg tgcagggcca gactggaggt   3840
ggcaacgcca atcagcaacg actgtttgcc cgccagttgt tgtgccacgc ggttgggaat   3900
gtaattcagc tccgccatcg ccgcttccac ttttcccgc gttttcgcag aaacgtggct   3960
ggcctggttc accacgcggg aaacggtctg ataagagaca ccggcatact ctgcgacatc   4020
gtataacgtt actggtttca cattcaccac cctgaattga ctctcttccg ggcgctatca   4080
tgccataccg cgaaaggttt tgcgccattc gatggtgtcc gggatctcga cgctctccct   4140
tatgcgactc ctgcattagg aagcagccca gtagtaggtt gaggccgttg agcaccgccg   4200
ccgcaaggaa tggtgcatgc aaggagatgg cgcccaacag tccccggcc acggggcctg   4260 ccaccatacc cacgccgaaa caagcgctca tgagcccgaa gtggcgagcc cgatcttccc   4320
catcggtgat gtcggcgata taggcgccag caaccgcacc tgtggcgccg gtgatgccgg   4380
ccacgatgcg tccggcgtag aggatcgaga tcgatctcga tcccgcgaaa ttaatacgac   4440
tcactatagg gaattgtga gcggataaca attcccctct agaaataatt ttgtttaact   4500
ttaagaagga gatatacata tgactccatt aggtcctgct tcttctctgc cgcaaagctt   4560
tctgctgaaa tgtctggaac aggttcgtaa atccagggt gacggtgctg cactgcaaga   4620
aaaactgtgc gctacttaca aactgtgcca tccggaagag ctggtactgc tgggtcattc   4680
tcttgggatc ccgtgggctc cgctgtcttc ttgtccatct caagctcttc agctggctgg   4740
ttgtctgtct caactgcatt ctggtctgtt cctgtatcag ggtcttctgc aagctctgga   4800
aggtatctct ccggaactgg gtccgactct ggacactctg cagctagatg tagctgactt   4860
tgctactact atttggcaac agatggaaga gctcggtatg gcaccagctc tgcaaccgac   4920
tcaaggtgct atgccggcat tcgcttctgc attccagcgt cgtgcaggag gtgtactggt   4980
tgcttctcat ctgcaatctt tcctggaagt atcttaccgt gttctgcgtc atctggctca   5040
gccgtaataa gctcgagcac caccaccacc accaccacca ctaattgatt aatacctagg   5100
ctgctaaaca aagcccgaaa ggaagctgag ttggctgctg ccaccgctga gcaataacta   5160
gcataacccc ttggggcctc taaacgggtc ttgaggggtt ttttgctgaa aggaggaact   5220
atatccggat ctag                                                     5234
```

<210> SEQ ID NO 5
<211> LENGTH: 46
<212> TYPE: DNA
<213> ORGANISM: Artificial Sequence
<220> FEATURE:
<223> OTHER INFORMATION: Primer sequence IntLambd 1

<400> SEQUENCE: 5
gtccgactta tgcccgagaa gatgttgagc aaacttatcg cttatc          46

<210> SEQ ID NO 6
<211> LENGTH: 44
<212> TYPE: DNA
<213> ORGANISM: Artificial Sequence
<220> FEATURE:
<223> OTHER INFORMATION: Primer sequence IntLambd 2

```
<400> SEQUENCE: 6
tgcaaagaga ttcttggcgg agaaaccata attgcatcta ctcg          44
```

METHOD FOR THE PRODUCTION OF POLYPEPTIDES

RELATED APPLICATION

This application is a national stage filing under 35 U.S.C. §371 of international application PCT/EP2013/055529, filed Mar. 18, 2013, which was published under PCT Article 21(2) in English, the disclosure of which is incorporated by reference herein in its entirety.

FIELD OF INVENTION

The present invention relates to the field of polypeptide production, in particular to the production of recombinant polypeptides in host cells that produce the recombinant polypeptide in inclusion bodies.

BACKGROUND

The expression of recombinant polypeptides in host cells is a standard technology widely used in biotechnology and the pharmaceutical industry. Especially microbial hosts, like for example *E. coli*, are commonly used, since relatively simple expression systems and cell culture conditions are available for these host cells. In general the cultivation process is therefore comparably economic.

It is, however, often difficult to obtain a polypeptide of interest in soluble and active form when it is expressed in microbial cells. Often, expression of a recombinant polypeptide leads to the production of poorly soluble intracellular aggregates of the polypeptide in denatured form, the so-called inclusion bodies [Baneyx, F. and Mujacic, M. (2004) Nat. Biotechnol. 22, 1399-1408 and Sorensen, H. P. and Mortensen, K. K. (2005) Microb. Cell Fact. 4, 1], also referred to as classical inclusion bodies.

Classical inclusion bodies are generally easy to isolate, typically by centrifugation at moderate speed. To recover the active, i.e. correctly folded, polypeptide from the inclusion bodies, the inclusion bodies have to be solubilized and the protein renaturated after isolation. Several patent applications and patents deal with the aspect of solubilizing the inclusion bodies and renaturing the proteins obtained from inclusion bodies. For example EP0512097, EP0364926, EP0219874, WO01/87925, Rudolph 1996, Rudolph 1990, Marston 1986 and Dietrich 2003 describe general techniques relating to the solubilization and renaturing of denatured proteins. For example, EP0219874 discloses generic methods for refolding of recombinant proteins from *E. coli* inclusion bodies. For the solubilisation the chaotropic agents GuHCl and arginine were used at high pH. EP0219874 describes the formation of disulfide bridges under redox conditions provided by GSH/GSSG.

Despite the fact that numerous processes for the isolation and solubilization of inclusion bodies are known, the results are not always satisfactory. One major problem is that the structure of the inclusion bodies can vary. It is known that the formation and the structure of the inclusion bodies can be influenced by parameters of the cell culture process, including for example media composition, growth temperature and production rate. WO2004/015124 describes the formation of "non-classical" inclusion bodies by modulating culture conditions.

Obtaining recombinant proteins from inclusion bodies, in particular in active form and sufficient amounts, can be problematic. Sometimes the structure of the inclusion bodies is too "soft" which leads to the situation that the isolation of the inclusion bodies by centrifugation is difficult. On the other hand it is also possible that the inclusion bodies are too compact. This results in inclusion bodies which cannot be solubilized even under rough conditions.

To overcome these disadvantages the present invention provides new cell culture processes which lead to large amounts of properly folded protein in inclusion bodies that can easily be isolated and solubilised, resulting in increased yield of the recombinant protein.

SUMMARY OF INVENTION

The present invention relates to the field of polypeptide production, in particular to the production of recombinant polypeptides in host cells that produce the recombinant polypeptide in inclusion bodies. The present invention provides a new method for the production of recombinant polypeptides from inclusion bodies which results in improved yields of active protein. The present inventors demonstrate herein that modulation of the cell culture conditions positively affects the yield of the recombinant polypeptide in active form. For example, the inventors have found that a two step culturing method involving a first higher cultivation temperature and a second lower cultivation temperature is beneficial. Other culture parameters are being described herein that also positively affect cell growth and expression of recombinant polypeptide in microbial host cells.

In one aspect, the invention provides a method for the production of a recombinant polypeptide in inclusion bodies, the method comprising
(a) cultivating a microbial host cell at a first temperature, the host cell comprising a nucleic acid encoding said recombinant polypeptide,
(b) lowering the cultivation temperature from the first temperature to a second temperature, and
(c) cultivating the microbial host cell at the second temperature.

The microbial host cell may be an *E. coli* cell. The first temperature may be between 36° C. and 38° C., preferably 37° C. The second temperature may be between 25° C. and 36° C., more preferably between 30° C. and 36° C., and more preferably between 32° C. and 35° C. The pH during cultivation at the first temperature and/or the second temperature may be between 6 and 8, preferably between 6.8 and 7.2.

In some embodiments, the lowering of the temperature is performed when the cell culture has reached an optical density at 600 nm of between 10 and 50, more preferably between 27 and 33.

In some embodiments, the recombinant polypeptide is a four-helix-bundle polypeptide. The recombinant polypeptide may be G-CSF. In some embodiments, the G-CSF is human or bovine G-CSF, optionally with an initial methionine amino acid residue at position −1, respectively.

In some embodiments, the nucleic acid is operably linked to an inducible promoter. The nucleic acid may be comprised in a vector, such as an expression vector. In some embodiments, steps (a) to (c) are preceded by a step of introducing into a host cell an expression vector comprising a nucleic acid encoding said recombinant polypeptide, wherein the nucleic acid is operably linked to an inducible promoter.

The inducible promoter may be a T7 promoter. The chromosome of the microbial host cell may comprise a nucleic acid sequence coding for a bacteriophage RNA polymerase, optionally operably linked to a lac promoter, and may be free of lysogenic bacteriophage nucleic acid sequences. The bacteriophage RNA polymerase may be T7 polymerase.

In some embodiments, expression of the recombinant polypeptide is performed by addition of an inducer. The inducer may be added simultaneously with or subsequently to lowering the temperature. The inducer may be IPTG.

In preferred embodiments, the vector comprises the sequence of SEQ ID NO:4.

In some embodiments, the nucleic acid encoding said recombinant polypeptide is selected from the group consisting of (i) a nucleic acid sequence encoding the polypeptide of SEQ ID NO:3 or SEQ ID NO:1, or (ii) a nucleic acid sequence encoding a polypeptide having a sequence identity of at least 90% to the sequence as depicted in SEQ ID NO:3.

BRIEF DESCRIPTION OF FIGURES AND TABLES

Table 1: Yield of G-CSF from cell culture with varied second cultivation temperatures Table 2: List of preferred conditions for downstream processing including two refolding steps.

Table 3: Purity and yields of three production runs starting with 650 g washed and frozen inclusion bodies. The calculation of yields refers to the moist mass of the inclusion bodies.

Table 4: Values of total purity and of two selected process related impurities (sarkosyl, endotoxins) during the purification of G-CSF. The ranges indicate the results the analysis of three G-CSF production lots using different analytical methods.

Table 5: Purity and activity of three G-CSF production lots

FIG. 1A, Schematic drawing of the expression vector of example 1; FIG. 1B, Sequence of G-CSF expression vector, SEQ ID NO:4.

FIG. 2: SEC-HPLC chromatograms analysing the purity of a commercially available filgrastim drug product as a reference (3A) and the product purified as described herein (3B).

DESCRIPTION OF THE INVENTION

The present invention provides a method for the production of recombinant polypeptides, which are expressed in inclusion bodies in a host cell. A nucleic acid encoding the recombinant polypeptide is introduced into a host cell. The host cell is then cultivated to express the recombinant polypeptide, wherein the host cell forms inclusion bodies containing the recombinant protein. After a first cultivation period and during continuous cultivation, the cultivation temperature is changed from a higher to a lower temperature. Cultivation of the host cell is then continued at the lower temperature.

The present inventors demonstrate herein that modulation of the cell culture conditions positively affects the yield of the recombinant polypeptide in active form. The inventors have surprisingly found that lowering the temperature of the cell culture during the cultivation of the host cell leads to an increased yield of the recombinant protein. The inventors have also found that other parameters, such as the induction mode, the pH, the downstream processing, and in particular the choice of expression system, etc. can also exert a positive effect on the yield. A combination of preferred temperatures and preferred expression systems as described herein were found to be particularly beneficial.

While not being bound to any theory, the inventors believe that the modulation of the culture temperature as described herein optimises the structure of the inclusion bodies, increasing the amount of correctly folded protein in the inclusion bodies and thus facilitate the recovery of more active recombinant protein from the inclusion bodies. The inventors believe that the structure and composition of the inclusion bodies can be a limiting factor with respect to the yield of the renatured active polypeptide. The additional parameters described herein, such as the induction mode, the pH, the downstream processing, and in particular the expression system, further facilitate additional increases in yield. The various additional parameters described herein may be applied individually or may be combined by applying one or more of the parameters to the methods described herein. The methods described herein result in improved cell growth and improved recombinant polypeptide expression in microbial host cells.

In a first aspect of the invention, there is provided a method for the production of a recombinant polypeptide expressed in inclusion bodies, the method comprising the steps of (a) cultivating a cell culture of microbial host cells at a first temperature, the host cells comprising a nucleic acid encoding said recombinant polypeptide, (b) lowering the temperature of cultivation from the first temperature to a second temperature, and (c) cultivating the culture of microbial host cells at the second temperature. Lowering of the temperature is performed during continuous cultivation. The nucleic acid has been introduced into the host cells. The nucleic acid may be comprised in a vector. The nucleic acid may be linked to an inducible promoter.

As used herein, the terms "polypeptide" and "protein" are used interchangeably to designate a series of amino acid residues connected to the other by peptide bonds.

A "recombinant nucleic acid" is a nucleic acid that results from the use of molecular engineering techniques to create new combinations of genetic material, generating nucleic acids that would otherwise not be found in the biological organisms. Proteins that result from the expression of recombinant nucleic acid within living cells are referred to as "recombinant proteins" or "recombinant polypeptides", The recombinant nucleic acid, which encodes the recombinant protein, is introduced into a host cell. The "nucleic acid" as used in the methods herein may be a heterologous nucleic acid, i.e. a nucleic acid that is foreign to the host cell. Or the nucleic acid may be derived from the host and may encode a polypeptide which is naturally expressed by said host. For example, introducing a second copy may lead to increased expression. Or the nucleic acid sequence is put under a transcriptional control other than the transcriptional control normally found for this nucleic acid in the host. The protein in its recombinant form would thus be expressed at a different expression level, for example it may be over-expressed or under-expressed compared to its endogenous expression level.

The recombinant nucleic acid sequence encoding the protein of interest may be modified before it is introduced into a host cell, by one or more mutation(s), insertion(s), deletion(s) and/or substitution(s), as long as such modified sequence encodes an active protein that has the same biological function as said protein of interest (i.e. is a functional equivalent of the protein of interest). A recombinant nucleic acid sequence as referred herein also encompasses nucleic acid sequences originating from a different domain (empire) of organisms, such as from eukaryotes (of eukaryotic origin), such as e.g. human sequences, which have been modified according to the "codon usage" of a prokaryotic host in order to optimize expression in the host cell.

The present invention can be applied to any protein which is produced in inclusion bodies. Inclusion bodies are formed generally by relatively hydrophobic proteins (such as G-CSF), thus the present invention can be readily applied to relatively hydrophobic proteins, especially those which (similar to G-CSF) do not have too many disulphide bonds. The present invention may thus be particularly suitable for proteins that have similar properties than G-CSF, such as similar solubility, similar hydrophobicity, similar number of cysteine bonds, etc. In some embodiments the methods are applied to hydrophobic proteins.

In particular, the inventors have found that the so-called "helix bundle proteins", and especially the "four helix bundle proteins" show particular improved high expression rates with the methods described herein. All helix bundle proteins have a core structure in common. They possess several alpha helices in their secondary structure, which are usually orientated in parallel or anti-parallel formation to each other in the tertiary structure. Four helix bundle proteins are particularly suitable to be produced with the methods according to the present invention. Ricci et al, 2003 and Weber et al, 1980 describe common structures and members of the four helical bundle family of proteins. Non-limiting examples of helix bundle proteins, which are particularly suitable for the present invention, include G-CSF (granulocyte colony-stimulating factor), GM-CSF (granulocyte-macrophage colony-stimulating factor), M-CSF (macrophage stimulating factor), hGH (human growth hormone), interferons, such as IFN-alpha 2 (Interferon alpha 2) or Interferon beta, interleukins, such as IL-2 (Interleukin-2), IL-4 (Interleukin-4), IL-7 (Interleukin-7), or IL-9 (Interleukin-9), erythropoietin, leptin, MGDF (megakaryocyte growth and development factor), and other cytokines. In preferred embodiments, the recombinant polypeptide is selected from the group consisting of G-CSF, GM-CSF, M-CSF, hGH, IFN-alpha 2, IL-2, IL-4, IL-7, and IL-9. In more preferred embodiments, the recombinant polypeptide is selected from the group of G-CSF, GM-CSF and M-CSF.

The sequence of the nucleic acid encoding the recombinant protein may be codon-optimized for the expression in a microbial host cell, in particular *E. coli*.

In some preferred embodiments, the recombinant polypeptide is G-CSF. Human granulocyte colony-stimulating factor (hG-CSF) belongs to hematopoetic growth factors which has a decisive role in the formation of neutrophils. G-CSF is used in medicine in the field of hematology and oncology. Today, two forms of G-CSF for clinical use are on the market: lenograstim, which is glycosylated and is produced in mammalian cells, specifically a CHO cell line (Holloway C J (1994) Eur J Cancer 30A Suppl 3:S2-S6., EP 169566), and filgrastim, which is nonglycosylated and is produced in *E. coli* (EP 237545).

"G-CSF" as used herein in the context of the invention includes species orthologues of G-CSF, such as for example human G-CSF, bovine G-CSF, etc. The amino acid sequence of human G-CSF is (SEQ ID NO:1):

TPLGPASSLPQSFLLKCLEQVRKIQGDGAALQEKLCATYKLCHPEELVLL

GHSLGIPWAPLSSCPSQALQLAGCLSQLHSGLFLYQGLLQALEGISPELG

PTLDTLQLDVADFATTIWQQMEELGMAPALQPTQGAMPAFASAFQRRAGG

VLVASHLQSFLEVSYRVLRHLAQP which for example can be found in Holloway, 1994, or under Drugbank Accession No DB00099.

The amino acid sequence of bovine G-CSF is (SEQ ID NO: 2):

TPLGPARSLPQSFLLKCLEQVRKIQADGAELQERLCAAHKLCHPEELMLL

RHSLGIPQAPLSSCSSQSLQLRGCLNQLHGGLFLYQGLLQALAGISPELA

-continued

PTLDTLQLDVTDFATNIWLQMEDLGAAPAVQPTQG AMPTFTSAFQRRAG

GVLVASQLHRFLELAYRGLRYLAEP which can for example be found in FIG. 7 of U.S. Pat. No. 5,849,883, or PDE Accession No: 1BGC-A.

In some preferred embodiments the G-CSF is mammalian G-CSF. In particularly preferred embodiments, the polypeptide is human G-CSF [Drugbank Accession No: DB00099], bovine G-CSF, [PDB Accession No: 1BGC-A], or a functional variant thereof. In some preferred embodiments the recombinant polypeptide is methionyl-G-CSF (Met-G-CSF), such has human Met-G-CSF (r-met-hu-G-CSF=filgrastim).

The amino acid sequence of filgrastim is (SEQ ID NO:3):

MTPLGPASSLPQSFLLKCLEQVRKIQGDGAALQEKLCATYKLCHPEELVL

LGHSLGIPWAPLSSCPSQALQLAGCLSQLHSGLFLYQGLLQALEGISPEL

GPTLDTLQLDVADFATTIWQQMEELGMAPALQPTQGAMPAFASAFQRRAG

GVLVASHLQSFLEVSYRVLRHLAQP

Bovine G-CSF may also be provided as methionyl-bovine G-CSF.

"G-CSF" as used herein in the context of the invention includes functional variants of G-CSF. Reference to "variant" herein means reference to "functional variant", unless the context indicates otherwise. A variant of G-CSF protein refers to a protein that differs from the G-CSF protein sequence, but still has the same biological activity (functional variant). A "variant" of G-CSF protein refers to a protein which differs from the reference G-CSF protein sequence (such as the human G-CSF sequence) in one or more amino acid(s). A "variant" may, alternatively or in addition, have other modifications such as, for example, methylation, pegylation, succinylation, addition of tags or labels, etc. The variant may be an enzymatically or chemically modified G-CSF. It may be a fusion protein fused to another peptide or polypeptide. In preferred embodiments, the G-CSF is pegylated.

Variants may be natural variants (see for example Zsebo 1986), including allelic variants, or synthetically generated variants. It was shown in the prior art that modified forms of G-CSF are expressed in inclusion bodies. Variants can thus be obtained using the improved methods described herein. For example, EP0719860 describes in examples 2 and 3 the construction and production of modified bovine G-CSF.

In some embodiments, the G-CSF variant is a protein sharing at least 70%, at least 80%, at least 90%, at least 91%, at least 92%, at least 93%, at least 94%, at least 95%, at least 96%, at least 97%, at least 98%, at least 99%, or at least 99.5% sequence identity with SEQ ID NO:3. (r-met-hu-G-CSF=filgrastim). Sequence identity can be determined using standard sequence analysis tools, such as for example Clustal, BLAST, etc. or alignment algorithms such as for example Needleman-Wunsch algorithm, Smith-Waterman algorithm, etc. The variant may have one or more conservative amino acid substitution(s). An amino acid substitution is conservative, if one amino acid is exchanged with an amino acid having similar properties, for example a polar amino acid with another polar amino acid, an acidic amino acid with another acidic amino acid, etc. Conservative substitutions are less likely to affect the chemical properties and thus the function of the protein. "Variants" to G-CSF thus include proteins having one or more mutation(s), deletion(s), substitution(s), insertion(s) and/or modification(s) of one or more amino acid compared to SEQ ID NO:3, as long as the variant of G-CSF still exhibit the same biological function than G-CSF (functionally equivalent). Whether a variant has the same biological function can be tested in assays determining the biological activity of G-CSF (see for example methods listed in Example 13). Commercially available G-CSF may be used as a reference control. A variant can be considered to have the "same biological activity", i.e. to be "biologically active" or "active" if it has at least 80%, at least 85%, at least 90%, at least 91%, at least 92%, at least 93%, at least 94%, at least 95%, at least 96%, at least 97%, at least 98%, at least 99%, or at least 99.5% of the activity of a commercially available G-CSF reference, such as filgrastim.

Reference to "G-CSF" herein thus includes reference to species orthologues and variants, i.e. functional variants, of human G-CSF.

Parameters that may be modulated during cell culture in accordance with the present invention include temperature, pH, optical density, dissolved oxygen level (DO), feed rate, carbon source, and other parameters that positively affect the yield of active recombinant protein.

Temperature

In some embodiments of the invention, the incubation temperature of the cell culture is lowered from a first higher temperature to a second lower temperature. The lowering of the temperature is performed during continuous cultivation of the host cells. At the lower temperature, the cells change from the growth phase to the production phase. In some embodiments, the first temperature is between 36° C. and 38° C. In preferred embodiments, the first temperature is between 36.5° C. and 37.5° C., or between 36.7° C. and 37.2° C., in more preferred embodiments the first temperature is about 37° C., in more preferred embodiments the first temperature is 37° C.

As used herein, if a range of values is referred to herein such as "between x and y", then the specific values x and y are included in the range, unless expressly specified otherwise.

The cell culture of host cells is incubated at the first temperature for the duration of a first cultivation period. The first cultivation period may be between 6 to 48 hours, but may be shorter or longer depending on the actual cell culture. In preferred embodiments, the first cultivation period may be 5 to 40 hours, or 10 to 36 hours, or 10 to 32 hours, or 14 to 28 hours, or 18 to 24 hours. In particular the first cultivation period may be 10, 12, 12.5, 14, 17, 18, 19, 20, 21, 22, 23, 24 hours, or may be a period defined by any combination of two of these values. The duration of the first cultivation period may also be determined based on the optical density of the cell culture (see below).

After the first cultivation period, the temperature is lowered, e.g. by simply resetting the fermentor temperature to a second lower temperature. In some embodiments the second temperature may be between 25° C. and 36° C., or between 26° C. and 36° C., or between 27° C. and 36° C., or between 28° C. and 36° C., or between 29° C. and 36° C. in preferred embodiments, the second temperature may be between 30° C. and 36° C., or between 30.5° C. and 36° C., or between 31° C. and 36° C., or between 32° C. and 36° C., or between 33° C. and 36° C., or between 34° C. and 36° C., or between 35° C. and 36° C., or between 30° C. and 35° C., or between 30.5° C. and 35° C., or between 31° C. and 35° C., or between 32° C. and 35° C., or between 33° C. and 35° C., or between 34° C. and 35° C., or between 30° C. and 34° C., or between 30.5° C. and 34° C., or between 31° C. and 34° C., or between 32° C. and 34° C., or between 33° C. and 34° C. In preferred embodiments, the second temperature may is 30° C., 30.5° C., 31° C., 32° C., 33° C., 34° C., 35° C. or 36° C., or may be within a range defined by any combination of two of these temperatures. Preferably, the second incubation temperature is between 30° C. and 35° C. or between 30° C. and 34° C. More preferably, the second incubation temperature is between about 31° C. and about 34° C., or between 31° C. and 34° C., more preferably between 31° C. and 33° C. Most preferably, the second incubation temperature is about 32° C. or is 32° C.

The cell culture of host cells is incubated at the second temperature for the duration of a second cultivation period. The second cultivation period may be between 1 to 20 hours, but may be shorter or longer depending on the actual cell culture. in preferred embodiments, the second cultivation period may be 1 to 20 hours, or 2 to 16 hours, or 3 to 14 hours, or 3 to 10 hours, or 3 to 8 hours, or 3 to 6 hours, or 4 to 14 hours, or 4 to 10 hours, or 4 to 8 hours, or 4 to 6 hours, preferably 5 hours. In particular the second cultivation period may be 1, 2, 3, 4, 5, 6, 7,8, 9, 10, 11, 12, 13, 14, 15, 16, 17, 18, 19 or 20 hours, or may be a period defined by any combination of two of these values.

pH

The pH may be maintained during the first and/or second cultivation temperature/period within specific values. The inventors have found that a pH between 6 and 8 is particularly beneficial and further promotes a high yield of the expressed protein, with a pH between 6.8 and 7.2 being particularly preferred. The methods described herein may thus comprise one or more step(s) of measuring the pH. The pH may be maintained during the first and/or second cultivation temperature/period within a range of between 6 and 8, or 6.5 and 7.8, or 6.6 and 7.4, or 6.7 and 7.3, or 6.8 and 7.2, or 6.9 and 7.1, or 6.9 and 7.0; or 6.6 and 7.2, or 6.7 and 7.2, or 6.8 and 7.2, or 6.9 and 7.2, or 7.0 and 7.2, or 7.1 and 7.2; or 6.6 and 7.1, or 6.7 and 7.1, or 6.8 and 7.1, or 6.9 and 7.1, or 7.0 and 7.1; or 6.6 and 7.0, or 6.7 and 7.0, or 6.8 and 7.0, or 6.9 and 7.0. The pH may be maintained during the first and/or second cultivation temperature/period within a range of between 6.8 and 7.2, or between 6.9 and 7.2, or between 7.0 and 7.2, or between 7.1 and 7.2; or between 6.8 and 7.3, or between 6.9 and 7.3, or between 7.0 and 7.3, or between 7.1 and 7.3, or between 7.2 and 7.3; or between 6.8 and 7.7, or between 6.9 and 7.7, or between 7.0 and 7.7, or between 7.1 and 7.7, or between 7.2 and 7.7, or between 7.3 and 7.7, or between 7.4 and 7.7, or between 7.5 and 7.7, or between 7.6 and 7.7. In particular the pH may be (about) 6.8, 6.9, 7.0, 7.1, 7.2, or may be a range defined by any combination of two of these values. The pH at the first cultivation temperature/period may be different from the pH at the second cultivation temperature/period.

Optical Density

The cultivation temperature may be lowered from a first to a second temperature depending on the optical density of the cell culture. The inventors have found that changing the temperature depending on the optical density can have an additional positive effect on the yield of the expressed protein. A lowering of the temperature when the OD at 600 nm is between 10 and 50 has been found to be beneficial, between and 33 particularly beneficial. The methods described herein may thus comprise a step of measuring the optical density (OD). The temperature may be decreased from the first to the second cultivation temperature when the cell culture reaches an optical density at 600 nm of between 10 and 50, or between 15 and 45, or between 20 and 40, or between 24 and 36, or between 27 and 33. The temperature may be decreased from the first to the second cultivation temperature when the cell culture reaches an optical density at 600 nm of between 27 and 32, or 27 and 31, or 27 and 30, or between 27 and 29 or between 27 and 28; or between 28 and 32, or between 28 and 31, or between 28 and 30, or between 28 and 29; or between 29 and 32, or between 29 and 32, or between 29 and 31, or between 29 and 30, or between 30 and 32, or 30 and 31, or between 31 and 32. The temperature may be decreased from the first to the second cultivation temperature when the cell culture reaches an optical density at 600 nm of 25, 26, 27, 28, 29, 30, 31, 32, 33, 34 or 35, or a density defined by any combination of two of these values.

Expression System/Vector/Host Cell

For expression the recombinant polypeptide is expressed in a host cell. In some embodiments steps (a), (b) and (c) of the method described above may thus be preceded by a step of introducing a nucleic acid into the host cell, wherein the nucleic acid encodes the recombinant polypeptide of interest. The nucleic acid may be introduced as part of a vector. In some embodiments the method is performed with a host cell which already contains the recombinant nucleic acid.

Various expression systems and expression vectors suitable for the recombinant expression of a protein in microbial cells are known. Any suitable expression vector and expression system may be used. A "vector" or "expression vector" is a polynucleic acid construct, generated recombinantly or synthetically, with a series of specified polynucleic acid elements that permit transcription of a particular nucleic acid sequence in a host cell. Typically, a vector includes a transcriptional unit comprising a particular nucleic acid sequence to be transcribed operably linked to a promoter. The promoter may be an inducible promoter, which can be activated by an external stimulus, such as addition of an agent, temperature, etc. A vector generally comprises a "transcription initiation region", a "transcription termination region", and may comprise an "enhancer". A vector expressible in a host can be e.g. an autonomously or self-replicating plasmid, a cosmid, a phage, a virus or a retrovirus. Examples of suitable vectors include pBR322 (Fermentas), pET300 vectors, pDEST vectors, and pET39b vectors (Novagen) and derivatives thereof. Further suitable expression vector can be taken from the Laboratory handbook "Sambrook and Russel, Molecular Cloning—A Laboratory Manual, $3^{rd}$ edition 2001, Cold Spring Harbor Laboratory Press, Cold Spring Harbor, NY, Chapter 15". In some embodiments, the vector is integrated into the genome of the host cell, i.e. integrative vector. In some embodiments, the vector is not integrated into the genome and is maintained separately in the cell, i.e. autonomous or binary vector.

"Promoter" as used herein refers to a nucleic acid sequence that regulates expression of a transcriptional unit. A "promoter region" is a regulatory region capable of binding RNA polymerase in a cell and initiating transcription of a downstream (3' direction) coding sequence. The promoter region generally comprise protein binding domains (consensus sequences) responsible for the binding of RNA polymerase, such as the putative −35 box and the Pribnow box (−10 box). Further, the promoter region may comprise the transcription start site and binding sites for regulatory proteins.

"Transcription initiation region" is a signal region which promotes transcription initiation and which comprises the sequence for the ribosome binding site, such as the Shine Dalgarno sequence. Typically the transcription initiation region is located downstream to the transcription initiation site and is operably linked to the nucleic acid(s)/gene(s) to be expressed.

"Transcription termination region" refers to a sequence which causes the RNA polymerase to terminate transcription. The transcription termination region is usually part of a transcriptional unit which can avoid unwanted transcription of other nearby nucleic acids/genes or transcription from other potential promoters and can increase the stability of the mRNA.

An "enhancer" is a nucleic acid sequence that acts to potentiate the transcription of a transcriptional unit independent of the identity of the transcriptional unit, the position of the sequence in relation to the transcriptional unit, or the orientation of the sequence. The vectors which may be used in accordance with the present invention optionally may include enhancers.

A nucleic acid sequence is "operably linked" when it is placed into a functional relationship with another nucleic acid sequence. For example, a promotor is operably linked to a coding sequence if it affects the transcription of the sequence; or a transcription initiation region such as a ribosome binding site is operably linked to a nucleic acid sequence encoding, e.g. a polypeptide, if it is positioned so as to facilitate transcription of the nucleic acid. Linking can be accomplished e.g. by ligation at convenient restriction sites.

"Nucleic acid" or "nucleic acid sequence" or "isolated and purified nucleic acid or nucleic acid sequence" as referred to herein might be DNA, RNA, or DNA/RNA hybrid. In case the nucleic acid or the nucleic acid sequence is located in a vector, it is usually DNA. DNA which is referred to herein can be any polydeoxynuclotide sequence, including, e.g. double-stranded DNA, single-stranded DNA, double-stranded DNA wherein one or both strands are composed of two or more fragments, double stranded DNA wherein one or both strands have an uninterrupted phosphodiester backbone, DNA containing one or more single-stranded portion(s) and one or more double stranded portion(s), double-stranded DNA wherein the DNA strands are fully complementary, double-stranded DNA wherein the DNA strands are only partially complementary, circular DNA, covalently-closed DNA, linear DNA, covalently cross-linked DNA, cDNA, chemicals-synthesized DNA, semi-synthetic DNA, biosynthetic DNA, naturally-isolated DNA, enzyme-digested DNA, sheared DNA, labeled DNA, such as radiolabeled DNA and fluorochrome-labeled DNA, DNA containing one or more non-naturally occurring species or nucleic acid. DNA sequences can be synthesized by standard chemical techniques, for example, the phosphotriester method or via automated synthesis methods and PCR methods. The purified and isolated DNA sequence may also be produced by enzymatic techniques. RNA which is referred to herein can be e.g. single-stranded RNA, cRNA, double-stranded RNA, double-stranded RNA wherein one or both strands are composed of two or more fragments, double-stranded RNA wherein one or both strands have an uninterrupted phosphodiester backbone, RNA containing one or more single-stranded portion(s) and one or more double-stranded portion(s), double-stranded RNA wherein the RNA strands are fully complementary, double-stranded RNA wherein the RNA strands are only partially complementary, covalently crosslinked RNA, enzyme-digested RNA, sheared RNA, mRNA, chemically-synthesized RNA, semi-synthetic RNA, biosynthetic RNA, naturally-isolated RNA, labeled RNA, such as radiolabeled RNA and fluorochrome-labeled RNA, RNA containing one or more non-naturally-occurring species of nucleic acid.

The expression system may be an inducible expression system, i.e. the expression of the recombinant polypeptide may be dependent on the presence of an. inducer. The nucleic acid encoding the recombinant protein may be operably linked on the expression vector with an inducible promoter. The relevant inducer may be supplied directly, for example by adding it or applying it to the cell culture, or it may be supplied indirectly, i.e. via a second construct within the host cell. Such a second construct in the host cell can, upon induction, produce a signal to induce expression of the nucleic acid.

The second construct may be part of the genome of the microbial host cell, or may be maintained autonomously within the cell.

Inducible expression systems are well known in the art. Known inducers include, for example, IPTG, lactose, NaCl, temperature etc. Particularly preferred in the methods described herein is induction with IPTG. If IPTG is used as an inducer, it may be used at a concentration in the range from 0.1 mM to 1 mM, more preferably from 0.2 to 0.6 mM, more preferably from 0.25 to 0.5 mM, more preferably from 0.3 to 0.35 mM, more preferably at a concentration of 0.33 mM.

In preferred embodiments, the expression vector comprises the nucleic acid encoding the recombinant polypeptide operably linked to an inducible promoter, preferably a T7 promoter. Expression of the nucleic acid is triggered by the presence of the inducer. In the case of the T7 promoter, expression is triggered by the presence of T7 DNA dependent RNA polymerase. In preferred embodiments, the expression vector may comprise or consist of the sequence of SEQ ID NO:4.

Corresponding to such an expression vector, the host cell may contain a suitable expression system. For example, the chromosome of the microbial host cell may comprise a nucleic acid for a bacteriophage RNA polymerase, such as the T7 RNA polymerase. The bacteriophage RNA polymerase may be operably linked to an inducible promoter, such as for example a lac promoter (lacZ protein beta-galactosidase promoter). The lac promoter can be induced by adding IPTG (isopropyl-1-thio-β-D-thiogalactopyranoside) to the host cell. The chromosome of the microbial host cell preferably is free of lysogenic bacteriophage nucleic acid sequences. The inventors have found that the use of such an expression system/expression vector is particularly beneficial in the methods described herein and leads to high yields of the recombinant protein obtained from the inclusion bodies. In particular, the inventors have found that using this expression system/expression vector in combination with a cultivation scheme as described herein, i.e. (i) cultivating said microbial host cell at a first temperature, the host cell comprising a nucleic acid encoding said recombinant polypeptide, (ii) lowering the cultivation temperature from the first temperature to a second temperature, and (iii) cultivating the microbial host cell at the second temperature, is particularly beneficial.

Thus, in one aspect of the invention, there is provided a method for the production of a recombinant polypeptide, which is produced in inclusion bodies (in a host cell), the method comprising the steps of (i) introducing into a host cell an expression vector comprising a nucleic acid encoding a recombinant polypeptide, wherein the nucleic acid is operably linked to a promoter, preferably an inducible promoter, (ii) cultivating said microbial host cell at a first temperature, the host cell comprising a nucleic acid encoding said recombinant polypeptide, (iii) lowering the cultivation temperature from the first temperature to a second temperature, and (iv) cultivating the microbial host cell at the second temperature. The inducible promoter may be a T7 promoter. The chromosome of the microbial host cell may comprise a nucleic acid sequence coding for a bacteriophage RNA polymerase, optionally operably linked to an inducible promoter such as for example a lac promoter, and is free of lysogenic bacteriophage nucleic acid sequences. The bacteriophage RNA polymerase may be T7 polymerase. The expression of the polypeptide is performed by addition of an inducer (such as for example IPTG).

It was surprising to find that the above described expression system works particularly well with the methods described herein. In the art induction with high temperature was often described as the most common induction mechanism. The present inventors, however, found that using a T7 driven expression system as described above in combination with the two-temperature culturing method described herein results in particular improvements regarding the yield of the expressed protein in active form.

In most preferred embodiments, the host cell's genome comprises a nucleic acid encoding bacteriophage RNA T7 polymerase operably linked to a lac promoter and is free of lysogenic bacteriophage nucleic acid sequences. The vector comprises a nucleic acid encoding the recombinant polypeptide, wherein the nucleic acid is operably linked to a T7 promoter. Upon addition of IPTG, the lac promoter induces expression of T7 Polymerase, which then induces expression of the recombinant protein via the T7 promoter.

The inventors have found that adding the inducer at a specific point during incubation, such as simultaneously or subsequently to lowering the cultivation temperature from the first to the second lower cultivation temperature, further promotes a high yield of the recombinant protein obtained from the inclusion bodies. The inducer may be added simultaneously or subsequently to lowering the cultivation temperature from the first to the second lower cultivation temperature. In other words, the inducer may be added at the time point when the temperature is being lowered, or it may be added later, i.e. during the second cultivation period at the second cultivation temperature. Preferably, the inducer is added at the time point when the temperature is being lowered.

Introducing the Nucleic Acid into the Host Cell

The expression vector containing the recombinant polypeptide of interest may be introduced into a host cell using standard techniques known in the art.

The terms "transformation", "transformed" or "introducing a nucleic acid into a host cell" denote any process wherein an extracellular nucleic acid like a vector, with or without accompanying material, enters a host cell. The term "cell transformed" or "transformed cell" refers to a cell or its progeny into which the nucleic acid has been introduced and which thus harbours the nucleic acid. The nucleic acid might be introduced into the cell so that the nucleic acid is replicable either as a chromosomal integrant or as an extra chromosomal element. Transformation of appropriate host cells with e.g. an expression vector can be accomplished by well known methods such as microinjection, electroporation, particle bombardment or by chemical methods such as Calcium phosphate-mediated transformation, described e.g. in Maniatis et al. 1982, Molecular Cloning, A laboratory Manual, Cold Spring Harbor Laboratory or in Ausubel et al. 1994, Current protocols in molecular biology, John Wiley and Sons.

Host Cell

Any microbial cell that allows for expression of a recombinant protein in inclusion bodies may be used in accordance of the invention. Microbial cells that produce inclusion bodies of recombinant protein include, for example, bacterial and yeast cells and filamentous fungus cells. The "host cell" or "host" may be any microbial cell, such as a bacteria, yeast or filamentous fungus cell. Bacteria cells are preferred host cells, with gram-negative bacteria being particularly preferred. Examples include cells such as C2523, 02523, and BL21(DE3) (all New England Biolabs). A particularly preferred host cell is an $E.\ coli$ cell. Suitable host cells for particular expression systems have also been described above.

The terms "host", "host cell" and "recombinant host cell" are used interchangeably herein to indicate a microbial cell into which one or more vectors or an isolated and purified nucleic acid sequence have been introduced. The use herein of the singular form "host cell" also indicates that a plurality of cells may be used, unless the context indicates otherwise. In practice, in the production of a recombinant host cell, a plurality of the host cell is used in the cell culture.

The term "isolated and purified nucleic acid sequence" refers to the state in which the nucleic acid sequence will be free or substantially free of material with which it is naturally associated such as other nucleic acids with which it is found in their natural environment, or the environment in which they are prepared (e.g. cell culture) when such preparation is by recombinant technology practiced in vitro or in vivo.

It is understood that the terms "host", "host cell" and "recombinant host cell" refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein, as long as they produce an active form of the recombinant protein or a functional variant thereof (see discussion on functional variants above).

In case the host is from a prokaryotic species, the recombinant nucleic acid sequence may originate from a different genus or family, from a different order or class, from a different phylum (division) or from a different domain (empire) of organisms.

The transformed host cells may be frozen and stored. A master cell bank and a working cell bank may be prepared, and tested for viability, identity, purity and stability.

Further Cell Culture Conditions

General set ups and culture conditions for culturing microbial cells are well established and will only be summarized here. Standard cell culture parameters may be adjusted based on common general knowledge in the art.

The cell culture medium is inoculated with a sample of the transformed microbial host cell. Suitable culture media are known in the art, including for example GBA medium, SOC (Super optimal carbon) medium, LB (Luria) medium, or RBY medium. Various amounts of culture medium may be inoculated. The culture may be a small-scale culture for example for laboratory use, for example 1 ml to 1 L of culture medium. The described methods are also particularly useful for large volumes up to industrial scale, i.e. preparative scale. The methods describe herein may thus be performed with larger cell culture volumes, including large-scale processing for industrial use. The culture may be in the range of 1-5 L, or 1-10 L, or 1-100 L, or 1-500 L, or 1-1000 L or more. The culture may be in the range of 5-5000 L, or 10-5000 L, or 50-5000 L, or 100 to 5000 L, or 5-1000 L, or 10-1000 L, or 50-1000 L, or 100-1000 L.

In some embodiments, first a seed culture is inoculated. The seed culture is cultivated until a specified optical density is achieved. The seed culture may be cultivated until the optical density at 600 nm is within the range of between 0.5 and 1.5, or between 0.6 and 1.4, or between 0.7 and 1.3, or between 0.8 and 1.2, or between 0.9 and 1.1. A preferred optical density is within the range of between 0.9 and 1.1.

The seed culture may then be transferred to a larger bioreactor with fresh medium.

The skilled person will be aware that it is necessary to monitor, for example, dissolved oxygen levels and nutrients in the cell culture to ensure efficient cell growth.

The feed rate may be linear. In some embodiments, when the dissolved oxygen (DO) level starts to increase steeply from the set-point, caused by exhaustion of the carbon source, linear feed addition may be started. The DO setpoint may be between 10% and 50%, between 20% and 45%, between 30% and 45%, between 35% and 45%, between 37% and 42%, or between 39% and 40%. The DO may be 35%, 36%, 37%, 38%, 39%, 40%, 41%, 42%, 43%, 44% or 45%, or the DO may be any combination of two of these values. Preferably, the DO is 40%.

Suitable nutrients are known in the art. As carbon source a sugar alcohol, preferably glycerol, may be used in the medium. The inventors have found that glycerol as carbon source results in high growth rates and a high biomass. The composition of the feed medium may comprise inter alia amino acids (mainly L-methionine, L-glutamine and L-leucine) and minerals (e.g. salts, phosphate, sulfate). All materials used are from animal-free sources.

One or more antifoam agent(s) or selection agent(s) may be used. As antifoam agents PPG2000, JM633, SB2020 may be used. The fermentation broth can further comprise kanamycin monosulfate (an aminoglycoside antibiotic) as selection agent.

Further components may be present, depending on the actual host cells used.

Downstream Processing

"Downstream processing" comprises the further processing of the cells harvested from the culture. The cells contain the inclusion bodies with the recombinant protein.

After cultivation of the cell culture comprising the transformed host cells, the cells can be separated from the culture medium by using low speed centrifugation or separators. After lysis of the cells the inclusion bodies containing the recombinant protein are obtained. In some embodiments, the method described anywhere herein may thus further comprise a step of obtaining the inclusion bodies from the host cell(s).

The inclusion bodies may be obtained by standard methods. Processes for obtaining the inclusion bodies from host cells generally comprise lysis and disruption of the cells followed by centrifugation. The inclusion bodies may be obtained by harvesting the cells in a separator (e.g. at about 11 000 g, e.g. by centrifugation,), mechanically disrupting the cells, e.g. with a high pressure homogenizer (e.g. at about 1000 bar), and then separating the inclusion bodies from cell debris in a separator (e.g. at about 11 000 g, e.g. by centrifugation,). The pellet comprising a large proportion of classical inclusion bodies is usually washed with suitable buffers including detergents. The inclusion bodies may be stored in a suitable buffer. Suitable buffers are any biologically acceptable buffers, like for example phosphate-, citrate-, acetate-, tartrate buffer, or water. The inclusion bodies may be stored in a suitable buffer at −80° C. for at least 8 months or propagated further without a holding step.

For the isolation of G-CSF, washing of classical inclusion bodies with for example 1% deoxycholate (Zsebo K M et al (1986) Immunobiology 172:175-184. EP237545; U.S. Pat. No. 5,849,883) or with a solution of 1.0 M NaCl with added 0.1% Tween 80 (Gelunaite L et al (2000) J Chromatogr A 904:131-143) has been reported to be convenient.

After the inclusion bodies have been obtained, the recombinant protein must be solubilised from the inclusion bodies. In some embodiments, the method described anywhere herein may further comprise the steps of (i) obtaining the inclusion, bodies and (ii) obtaining the recombinant, protein from the inclusion bodies. The invention also provides a recombinant protein obtainable or obtained by the methods described herein.

Obtaining the inclusion bodies may be achieved using common techniques, as set out above. For the production of correctly folded biologically active proteins from inclusion bodies which are insoluble in common aqueous buffers or water based liquids under native conditions, the inclusion bodies are isolated from the cells, washed and solubilised, and then in vitro renaturation is performed.

Obtaining the recombinant protein from the inclusion bodies may be achieved using common techniques. For example, EP0219874 discloses generic methods for refolding of recombinant proteins from *E. coli* inclusion bodies. For the solubilisation the chaotropic agents GuHCl and arginine were used at high pH. EP0219874 describes the formation of disulfide bridges under redox conditions provided by GSH/GSSG. Methods for obtaining monomeric soluble G-CSF are for example described in Zsebo 1986, WO87/01132, Devlin 1988, Holloway 1994, WO01/04154, U.S. Pat. No. 5,055,555. Further processes were described in WO89/10932, Lu 1992, Heidari 2001, Wingfield 1988, Kang 1998, WO98/53072, Wang 2005, WO01/87925, WO2004/015124, WO2004/001056, WO2006/097944, WO2006/135176, EP1630173, EP1837346, Rao 2008, Khalilzadeh 2008, WO2008/096370, WO2010/146599.

For example WO89/10932 and EP0719860 describe a process for isolating and purifying recombinant G-CSF from a microorganism. The method described in WO89/10932 and EP0719860 comprises lysing the microorganism and separating insoluble material containing G-CSF from soluble proteinaceous material; solubilising and oxidizing the G-CSF in the presence of a solubilising agent and an oxidizing agent; removing the solubilising agent using a DOWEX ion exchange resin having a cross-linked styrene-divinylbenzene polymer matrix; subjecting the G-CSF to ion exchange chromatography; and recovering the purified G-CSF. The ion exchange chromatography may be an anion exchange chromatography (AEX) followed by a cation exchange chromatography (CEX). The cell lysis may be performed with a Gaulin homogenizer with subsequent centrifugation to collect the pellet. The washing of the inclusion bodies may be performed with, for example, deoxycholate or another bile salt or non-ionic detergent. The solubilising agent may be Sarkosyl, the oxidizing agent may be copper sulphate. Sarkosyl could then be removed using batch adsorption with Dowex or other ion exchange resin. Subsequent AEX and/or CEX chromatographies may then be used for, polishing.

Such a purification procedure allows to obtain G-CSF as a soluble, monomeric and correctly folded form from the inclusion bodies. The protein can be purified further using ion exchange chromatography in monomoric and oxidized form only. Aggregates, dimeric or otherwise incorrectly folded protein would precipitate and remain in filters and on the column. G-CSF is biologically active in correctly folded, monomeric form.

It can thus be assumed that monomeric solubilised G-CSF obtained from the methods described herein is correctly folded and thus biologically active. Biological activity of G-CSF may be tested using methods set out in Example 13. The inventors also describe herein a new and inventive downstream processing method, which may be used in combination with the up-stream cell culture (fermentation) methods described herein. It leads to further increased yields of correctly folded recombinant protein. The downstream processing methods comprise the steps of solubilising the recombinant protein, performing an oxidation and first refolding step, removing the solublising agent and performing a second refolding step. In particular, the culturing methods described herein may be performed in combination with a method for refolding the recombinant protein from inclusion bodies, comprising:

a) solubilising the recombinant protein in the presence of a solubilising agent;

b) performing an oxidation and first refolding step, comprising incubating the recombinant protein in the presence of an oxidizing agent and the solubilising agent;

c) removing the solubilising agent by ion exchange resin adsorption and/or ion exchange chromatography, and optionally performing an acid precipitation; and d) performing a second refolding step, comprising diluting and incubating the recombinant protein of step (c) in the absence of solubilising agent.

The inclusion bodies can be obtained from a microorganism, preferably from *E. coli*. The solubilising agent may be N-Lauroylsarcosin. The oxidizing agent may be $CuSO_4$. The solubilisation may be performed at a pH value greater than pH 7. The solubilising agent may be N-Lauroylsarcosin at a concentration of about 0.5% to about 1.5%. The oxidation and first refolding step may be performed for at least two hours. The oxidation and first refolding step may be performed under airflow and without cooling. The oxidation and first refolding step may be performed at a pH value of about 7-9 and/or at a temperature of about -28° C. and/or for about 15-25 hours.

The removal of the solubilising agent in step (c) above may comprise: AEX (anion exchange) and CEX (cation exchange), optionally in this order. The removal of the solubilising agent in step (c)above may comprise:

a) binding to an anion exchange resin material by mixing the recombinant protein solution with the suspended resin material and removal of the resin material by filtration, and/or b) ion exchange chromatography under conditions where the solubilising agent binds to the resin and the recombinant protein remains in the flow through and/or, c) ion exchange chromatography under conditions where the recombinant protein binds to the resin and the solubilising agent remains in the flow through.

The solubilising agent and other impurities may be removed by the sequential application of the following steps: AEX, acid precipitation, AEX, and CEX. The solubilising agent and other impurities may be removed by the sequential application of the following steps:

a) binding of the solubilising agent to an anion exchange resin material by mixing the recombinant protein solution with the suspended resin material and removal of the resin material by filtration;

b) precipitation of impurities by lowering the pH below pH 5 and by removal of the precipitate by filtration;

c) anion exchange chromatography conducted under conditions wherein the residual solubilising agent binds to the resin and the recombinant protein remains in the flow through;

d) cation exchange chromatography conducted under conditions wherein the recombinant protein binds to the resin and the residual solubilising agent remains in the flow through; and e) elution of bound recombinant protein from the cation exchange resin by step or gradient elution using an elution buffer with increased pH or salt concentration.

The second refolding step may be performed in a low conductivity buffer and/or under cooled conditions and/or for more than 12 hours. The second refolding step may be performed at a conductivity below 2.0 mS/cm, and/or at a temperature of about 2-8° C. and/or for at least 24 hours. The second refolding step may be performed at a pH value above pH 7.

The method for refolding the recombinant protein from inclusion bodies described above may further comprise a polishing step, which may comprise one or more ion exchange chromatographies. The one or more ion exchange chromatographies in the polishing step may comprise an anion exchange chromatography followed by a cation exchange chromatography.

The various steps are now being described:

Solubilisation: The recombinant of the IB fraction is solubilised in the presence of a solubilising agent. Any suitable solubilising agent may be used. Such solubilising agents can be selected from, for example, (but are not limited to) the group of a denaturant or a chaotropic agent, such as for example (but not limited to) GuHCl or urea, or the group of a detergent, a tenside or a surfactant, such as for example (but not limited to) N-lauroylsarcosin (sarkosyl), lauric acid, sodium dodecyl sulphate (SDS) or N-cetyltrimethylammonium chloride. In preferred embodiments, the solubilising is performed with sarkosyl at alkaline pH, preferentially pH 8, preferably at a concentration of sarkosyl of 0.2-2.0% (w/v), in more preferred embodiments about 0.5%-1% (w/v) and most preferably about 1% (w/v) or 1% (w/v). The preferred buffer for the solubilisation is Tris-HCl/pH 8, preferentially 40 mM Tris-HCl/pH 8. After the solubilisation, a dilution step may be performed, with water or low conductivity (i.e. a conductivity of at least below 2 mS/cm, more preferably below 1 mS/cm) buffer.

First Refolding (oxidative folding): A first oxidative refolding step is performed in the presence of the solubilising agent, such as sarkosyl, and an oxidizing agent, such as CuSO4 (or others such as oxygen or air flow (bubbling), GSSG (Glutathion-ox), metal ions (Cu2+, Fe2+, Zn2+, . . . ) peroxide (H2O2)), in effective amounts. The inventors found that in the presence of solubilising agent, such as sarkosyl, the folding of the recombinant protein was not fully achievable. The inventors have found that complete removal of the solubilising agent followed by a second folding step in the absence of solubilising agent leads to improved yield of recombinant protein.

Removal of solubilising and oxidising agent and removal of other contaminants: Any suitable removal method may be used, For example, sufficient removal can be achieved by ion exchange resin adsorption, and/or acid precipitation, and/or ion exchange chromatography. Applying any one or a combination of these techniques results in a concentration of the solubilising agent, such as sarkosyl, which will not interfere with refolding in the second refolding step, preferably below 0.01 mg/ml, preferably below detection limit. (The concentration of residual solublising agent may be measured by HPLC an detection by UV. The method is described in more detail in Burgess, R. R. 1996. Purification of over produced *E. coli* RNA polymerase c factors by solubilizing inclusion bodies and refolding from sarkosyl. Methods Enzymol. 273:145-149.) These purification steps may be applied in any order and/or in any combination, as long as it leads to a complete removal of the solubilising agent. Other suitable purification methods may also be used. The solubilising agent and other impurities may be removed by the sequential application of the following steps: AEX, acid precipitation, AEX, and CEX. Suitable materials and conditions to perform ion exchange resin adsorption, acid precipitation and ion exchange chromatography, such as AEX or CEX, are known in the art and are commercially available.

Second Refolding (completion of folding): The second refolding step comprises diluting, such as two fold with water or low conductivity buffer, and then incubating the partially refolded G-CSF, preferably in a mildly alkaline pH, such as pH 8. A preferred buffer for the second refolding step is Tris-HCl/pH 8, preferentially 10 mM Tris-HCl/pH 8.

Final purification (polishing step(s)); Further polishing steps may optionally be performed, optionally including AEX and/or CEX, until a desired degree of purity of the recombinant protein is achieved.

EXAMPLES

Example 1

Production of G-CSF
Material and Methods
1. Generation of a Host Cell Line
Preparation of T7 RNA Polymerase Cassette In order to isolate the 4.44 kb gene cassette containing the functional T7 RNA polymerase (Accession number AY264774, protein AAP33914.1] operably linked to the regulatory domains of the lac operon, the genomic DNA from the *Escherichia coli* BL21(DE3) strain (Novagene) was used. The DNA was prepared with the Quiagen Genomic tip-20 kit (Quiagen, Hilden, Germany) using a standard protocol. The T7 cassette was then amplified by PCR reaction. The amplification was carried out in a 100 µl reaction volume utilizing the KOD HiFi DNA Polymerase (Merck, Darmstadt, Germany). The reaction mixture contained DNA polymerase buffer, 5U KOD HiFi DNA polymerase, 2 mM MgCl2, 250 µM dNTPs, 100 ng DNA template, 10 µM forward primer (IntLambd 1), 10 µM backward primer (IntLambd 2). For the reaction a PCR cycler [MJ Research PTC-200] was used with the following settings: Denaturation at 98° C. for 30 s, followed by 35 cycles with 30 s at 98° C. (denaturation), 30 s at 65° C. (annealing), 2 min at 72° C. (synthesis). Final synthesis was performed for 10 min at 72° C.

The following primers from the Int gene of lambda-phage were used for the PCR reaction:

```
IntLambd 1:
                                      (SEQ ID NO: 5)
GTCCGACTTATGCCCGAGAAGATGTTGAGCAAACTTATCGCTTATC IntLambd 2:
                                      (SEQ ID NO: 6)
TGCAAAGAGATTCTTGGCGGAGAAACCATAATTGCATCTACTCG
```

The DNA was purified from the PCR solution with Millipore Montage PCR Cleanup Kit. Three volume gel solubilization solution from the Qiaquick Gel Extraction Kit was added to the reaction solution, then the samples were centrifuged. Afterwards 400 µl of water and gel solubilization solution mixture (mixed in 1:3 proportion) was added. After centrifugation the DNA retained on the filter was washed with 3×400 µl TE buffer and then the DNA was taken up in 45 µl of sterile water. 5 µl of BamHI buffer was added to the isolated PCR product and the mixture was digested with 10 units of BamHI restriction enzyme for 4 hours at 37° C. and then purified according to the procedure described above. The pBR322 plasmid was purified from XL1-Blue MRF cells using HiSpeed Plasmid. Midi Kit. 1 µg of the purified plasmid was digested with 5 units of BamHI enzyme for 4 hours at 37° C. in a 20 µl reaction mixture prepared with BamHI buffer. In order to avoid the self-closure of the vector, the phosphate group linked to the end was cleaved by digestion with 0.5 unit of BAP (bacterial alcalic phosphatase) enzyme (incubation for 30 minutes at 60° C.). The vector was separated in 1% TAE agarose gel and was purified by using Qiaquick Gel Extraction Kit. The purification was performed in accordance with the KIT protocol, and at the end the vector was eluted in 50 µl volume. The purified vector and the insert were mixed and treated with T4 DNA ligase overnight at 16° C. in 200 µl reaction mixture. After treatment the DNA was precipitated with 3 volumes of ethanol, and after evaporation it was dissolved in 50 µl of sterile water.

Generation of Integration Construct

For the introduction of the above isolated T7 RNA polymerase cassette into the chromosomal DNA of the modified BL21 E. coli strain C2523H (New England Biolabs) the above isolated T7 RNA polymerase cassette was cloned into the 705-pmj plasmid. This plasmid comprises a temperature sensitive replication origin.

In order to prepare the integration construct, the insert from the 4µ gpBR322/T7 plasmid, obtained from XL1-Blue MRF cells [Stratagene] using HiSpeed Plasmid Midi Kit, was cleaved by ClaI/SalI enzyme in 50 µl SalI buffer solution. The digestion continued 4 hours at 37° C. The digestion resulted in two fragments, the Cla/SalI fragment of the pBR322 and the T7 polymerase containing fragment.

The pLacZ vector was gained from the XL1-Blue MRF cells using HiSpeed Plasmid Midi Kit. The end of the LacZ gene was removed from the pLacZ vector by applying EcoRI/ClaI enzymes for 4 hours at 37° C. 2 µg of the DH5a [Invitrogen] transformed 705-pMJ plasmid [Gene Bridges GmbH] purified by using HiSpeed Plasmid Midi Kit was partially digested in EcoRI buffer with 0.01 unit EcoRI enzyme for 30 minutes. The partially digested plasmid DNA was purified by QIAquickGel Extraction Kit, then it was digested in SalI buffer with SalI enzyme for 4 hours at 37° C. and then the plasmid was dephosphorylated with 0.5 unit of BAP enzyme (bacterial alkaline phosphatase) for 30 minutes at 60° C.

The inserts and the vector were run on a 1% TAE agarose gel and were purified using QIAquick Gel Extraction Kit, respectively, then mixed and ligated for 16 hours in a 200 ml volume.

Afterwards the DNA was precipitated with ethanol, and after evaporation it was electroporated into DH5α cells containing the gene of RFP protein inserted into a pET3d. vector (for the multiplication of 705-pMJ plasmid and its derivatives DH5α cells were used in order to obtain it in the appropriate amount). Four of the red cells were multiplied and the plasmid was analysed whether it contains the whole insert. The construct obtained was designated as pMJ-LacI-LacUV-T7Pol-LacZ. Subsequently, the pMJ-LacI-LacUV-T7Pol-LacZ plasmid was purified with HiSpeed Plasmid Midi Kit (Quiagen)and then transformed into C2523 modified BL21 cells.

2. Generation of G-CSF Expression Vector and the Transformed Host Cell

G-CSF Expression Vector:

A specific expression vector for G-CSF was constructed. The 525 by long full length human cDNA sequence for N-(L-Methionyl) Granulocyte-Colony Stimulating Factor (metHuG-CSF) encodes for a protein identical to the 174 amino-acid isoform of human G-CSF with an additional N-terminal methionine residue as published for example in EP 0 401 384.

The expression construct was created by inserting the r-metHuG-CSF DNA [Accession number AR049895] into the NdeI-XhoI position of a modified pET39b vector (New England Biolabs), creating the pRG/GCSFa plasmid, as described in Sambrook, J., Fritsch, E. F., and Maniatis, T., Cold Spring Harbor Laboratory Press, NY, Vol. 1, 2, 3 (1989) and Glover, D. M., IRL Press, Oxford, 1985.

The 5234 by long pRG/GCSFa vector contains: antibiotic (kanamycin) resistance gene (Kan), position: 822-7, T7 promoter, synthetic r-metHuG-CSF gene (G-CSF), T7 terminator, lacI repressor (LacI), and a replication origin (Ori). A schematic overview of the vector is depicted in FIG. 1.

The vector was transformed into the host cell obtained under point 1 using electroporation.

3. Cell Culture 100 ml of sterile seed culture medium (RBY) were inoculated with the WCB (Working cell bank) bacterial cell suspension under aseptic conditions. The inoculated seed culture was incubated at 37° C. with constant agitation at 185 rpm for 24 hours. When the optical density of the seed culture reached optical density at 600 nm of 1.0, the seed culture is transferred to a 20 L bioreactor (with working volume 15 L). The inoculated seed culture was incubated for 18 hours at 37° C. with constant stirring at 400 rpm and aeration at a rate of L/min. When the optical density at 600 nm of the seed culture has reached about 0.9, the collected seed culture is transferred to a 1000 L bioreactor (with working volume 500 L) with GEA medium, containing synthetic component and glycerol as carbon source. The cultivation was performed under strict aerobic conditions (DO≥30%) in a submerged culture at 37° C. During the whole cultivation period the pH value was maintained at a range of 6.8-7.2.

When the dissolved oxygen (DO) level began to increase steeply from the set-point (DO=40%), linear feed addition was started. When the optical density of the culture have reached optical density at 600 nm of 30, the fermentation temperature was decreased to temperature 32° C. Subsequent to the lowering of the temperature IPTG was added to the culture to induce a high-level target protein expression. After 5 hours post induction period the fermentation was stopped by shutting down the carbon source feeding and decreasing the agitation and aeration, the cell culture was cooled below 15° C. and the cells were harvested. The main fermentation altogether was taken 21 hours.

As carbon source glycerol was used in the medium. Glycerol as carbon source resulted in high growth rates and a high biomass. The composition of the feed medium comprised amino acids (L-methionine, L-glutamine and L-leucine) and minerals (e.g. salts, phosphate, sulfate). All materials used were from animal-free sources. As antifoam agents SB2020 was used. The fermentation broth further comprised kanamycin monosulfate (an aminoglycoside antibiotic) as selection agent.

4. Midstream Processing

1. Preparation of Inclusion Bodies (IB)

After fermentation, preparation of the inclusion bodies was performed. Agitation, aeration and feeding of carbon sources were stopped, the culture was cooled below 15° C., and the bacteria were harvested by separation at 11 000 g. The cells sedimented in the rotor and were washed out (discharged) by water. The bacterial cell concentrate was collected, diluted back to half volume by water and 0.5M $NaH_2PO_4$ was added to a final concentration of 10 mM. The cells were disrupted under pressure (100 MPa) by passing through a homogeniser three times. Inclusion bodies were separated from cell debris by sedimentation in separator at 11 000 g. The sedimented inclusion bodies were discharged in washing buffer containing 5 mM DTT, 10 mM $NaH_2PO_4$, 5mM EDTA, and 2% Tween 20 at pH 7.2. The concentrated IB suspension was diluted 2-fold with the same buffer and sedimented again. This washing procedure was repeated two times using 10 mM $NaH_2PO_4$ buffer, at the end of the second procedure without dilution. The final sediment of IBs was stored frozen at −80° C. and was stable for 8 months.

After thawing of the inclusion bodies the G-CSF can be solubilised, refolded, and further purified by techniques well established in the arts. A suitable process is for example described in U.S. Pat. No. 5,849,883.

Results

Table 1 presents the results of the fermentation of the above described transformed host cell, wherein the first cultivation temperature was 37° C., and the second cultivation temperature was 25° C., 30° C., 32° C., 35° C. or 37° C., respectively.

The results clearly indicate that lowering the temperature during cultivation leads to an increased yield of solubized G-CSF. In particular, it is apparent that incubation at a second cultivation temperature of between 32° C. and 35° C. leads to an increased yield. A second incubation temperature of 32° C. was particularly effective.

Example 2

Fermentation and Expression

The G-CSF (filgrastim) was produced with the recombinant E. coli C2523 T7 pol pRG/GCSFa clone (E. coli transformed with an expression vector comprising G-CSF). Under aseptic conditions the prepared seed culture media was inoculated with 0.10-0.15 cm$^3$ cell suspensions obtained from a thawed working cell bank vial that was stored in liquid nitrogen. The inoculated seed culture flasks were incubated in a gyratory shaker incubator at 37° C. at 185 rpm for 24-28 hours. When the mean value of the optical density at 600 nm (OD) of the six shaked flask culture reached 0.9-1.1, the content of the flask was collected into a sterile 5 dm$^3$ glass flask equipped with a silicone tube. The collected 3 dm$^3$ volume seed culture was transferred with a WM323U/R pump to the 100 dm$^3$ fermenter filled up to 75 dm$^3$ with sterile and supplemented production medium (GBA, synthetic medium with glycerol as carbon source). The cultivation was performed under strict aerobic conditions in a submerged culture at 37° C. When the carbon source became exhausted from the medium, a glycerol feeding solution was added to the culture in appropriate rates. The dissolved oxygen tension was maintained at a level not less than 30% during the whole culture period. When the OD value of the culture reached 30, the temperature was decreased to 32° C. and 0.33 mM IPTG was added to induce the expression of G-CSF. The bacteria were further cultivated for producing G-CSF for 5 hours until an OD of 80-95.

Example 3

Harvest of Bacteria

Agitation, aeration and feeding of carbon sources were stopped, the culture was cooled below 15° C., and the bacteria were harvested by separation at 11000 g. The cells sedimented in the rotor and were washed out (discharged) by water. The bacterial cell concentrate was collected, diluted back to its half volume with water, and 0.5M NaH$_2$PO$_4$ was added to a final concentration of 10mM. The total mass of the wet bacterial cells (biomass) were about 10-11.5 kg.

Example 4

Lysis of Bacteria and Inclusion Bodies Preparation

The separated and washed bacteria were disrupted under pressure (100 MPa) by passing through a homogeniser three times. Inclusion bodies were separated from cell debris by sedimentation in separator at 11000 g. The sedimented inclusion bodies were discharged in washing buffer containing 5 mM DTT, 10 mM NaH$_2$PO$_4$, 5mM EDTA, and 2% Tween 20 at pH 7.2. The concentrated IB suspension was diluted 2-fold with the same buffer and sedimented again. This washing procedure was repeated two times using 10 mM NaH$_2$PO$_4$ buffer, at the end of the second procedure without dilution. The final sediment of IBs was stored frozen at −80° C.

Example 5

Solubilisaton of Inclusion Bodies

The frozen inclusion bodies (650 g moist mass) were thawed and dissolved in solubilisation buffer containing 40 mM Tris-HCl, pH 8 and 1% (w/v) N-lauroylsarcosin (sarkosyl) in a total volume of 32.5 dm$^3$. The suspension was incubated at room temperature under continuous stirring.

Example 6

Oxidative Refolding (1$^{st}$ Refolding)

The solubilised IB suspension was diluted 2-fold with water to 0.5% sarkosyl and 20 mM Tris-HCl as final concentrations in a total volume of 65 dm$^3$. CuSO$_4$ was added to a final concentration of 40 μM. G-CSF was oxidized and partially refolded during continuous stirring and airflow in the head space at room temperature for at least 20 hours. The oxidation was terminated by the addition of EDTA at a final concentration of 1 mM.

Example 7

Sarcosyl Removal by AEX Batch Adsorption

Sarkosyl was adsorbed to an anion exchange (AEX) resin in a batch mode. An amount of 20g AG 1-X8 resin (BioRad, USA) per gram sarkosyl was applied and added to the solution. The suspension was stirred for two hours to bind most of the sarkosyl. The resin was removed by filtration through a 100 μm pore size nylon bag filter mesh. The remaining sarkosyl in the filtrate was completely removed from the product with the subsequent purification steps (Examples 8 and 9).

Example 8

Precipitation of Contaminants at Acid pH

By acidic precipitation at pH 4.3-4.5 some impurities were easily removed while G-CSF remains soluble. Any potential non-specific and undesired co-precipitation of G-CSF was prevented by addition of 1M urea in final concentration. Urea was provided by a 6M stock solution and slowly added to the filtrate of Example 6 with a rate of 1 dm$^3$/min. Subsequently, the pH was decreased by adding $\frac{1}{20}$ volume of 1M sodium acetate pH 4.8. The pH was further lowered to 4.3-4.5 by titrating with 50% acetic acid. The precipitation was allowed for at least one hour. Then the precipitated material was removed by filtration through a depth filter (Pall K700/KS50 dual layer).

Example 9

Residual Sarkosyl Removal and Buffer Exchange by Series-Connected AEX+CEX Chromatographies Sodium acetate 50 mM/pH 4.5 buffer was used for equilibration of 1) a 4 dm$^3$ column packed with DEAE Macro-Prep (Bio-Rad, USA) AEX resin, and) an 8 dm³ column packed with Toyopearl SP-650C (Tosoh, Japan) CEX resin. Both columns were connected directly on an ÄKTA process chromatography system (GE Healthcare, Sweden) in a tandem arrangement. After clearance through a 0.2 µm sterile filter, the filtrate of Example 7 was loaded onto the first column. Residual sarkosyl bound to the DEAE resin, while G-CSF remained unbound (non-binding mode) and appeared in the flow-through of the first column. This flow through was loaded directly onto the second column (SP resin), which bound G-CSF (binding mode). A simple step elution with 20 mM Tris-HCl/pH 8 desorbed the G-CSF from the resin. Besides the removal of residual sarkosyl, a buffer exchange from Na-Acetate/pH 4.5 to Tris-HCl/pH 8 was also achieved by this method.

Example 10

2$^{nd}$Refolding (Completion of Folding)

At this stage the folding of about half of the protein fraction was completed, while the remaining protein was incompletely folded or misfolded. The G-CSF solution eluted from Toyopearl SP-6500 in 20 mM Tris-HCl, pH 8 and was passed through a 0.2µm sterile filter into a stainless steel vessel.

The filtered solution was diluted 2-fold with water. The second incubation for protein folding (2$^{nd}$ Refolding) was carried in a low conductivity environment (<1 mS/cm) at pH 8 under cooling at 2-8° C. for 32-42 hours.

Example 11

Purification by AEX Chromatography (Polishing Step 1)

A column was packed with DEAE Macro-Prep (Bio-Rad, USA) and was equilibrated with 10 mM Tris-HCl/pH8. The solution which resulted from the 2$^{nd}$ refolding (Example 9) was loaded to the DEAE column. The correctly folded G-CSF was eluted by an increasing linear NaCl gradient from 0 mM to 200 mM in 10 mM Tris-HCl/pH 8. The eluted G-CSF was pooled and diluted 2-fold with water. The pH was adjusted to 4.5 by titration with 50% acetic acid.

Example 12

Purification by CEX Chromatography (Polishing Step 2)

For the final polishing step the G-CSF pool collected from the AEX chromatography (Example 10) consisting of correctly folded protein was directly applied onto a CEX column packed with Toyopearl CM-650S resin. The column was equilibrated by 20 mM sodium acetate, pH 5.3. The bound G-CSF was eluted by an increasing linear salt gradient from 20 mM to 400 mM sodium acetate within 24 column volumes at pH 5.3. Fractions with pure G-CSF were collected and pooled for formulation.

Example Formulation of Purified G-CSF by Gel Chromatography

The purified G-CSF as eluted from the CEX column (Example 11) was filtered through a 0.2 µm sterile filter and passed through a 14 dm³ column packed with Sephadex G-25 fine resin equilibrated with formulation buffer (10 mM sodium acetate, pH 4, 5% sorbitol, and 0.006% polysorbate 80). The same buffer was used as running buffer. G-CSF eluted in the void volume in formulation buffer. For a whole batch (35-48 g G-CSF) three subsequent formulation runs on Sephadex G-25, each with one third of the filtered CEX eluate, were performed. The formulated G-CSF was adjusted to a concentration of 0.9-1.0 mg/ml by dilution with formulation buffer, and finally filtered through a 0.2 µm sterile filter capsule. Formulated G-CSF as sterile solution is very stable and can be stored at 2-8° for many months if not years.

Example 13

Analytical Methods

Well-known standard analytical methods were performed in compliance with the European Pharmacopoeia (Ph. Eur.), which contains a monograph for filgrastim describing specific analytical methods (European Directorate for the Quality of Medicines & Health Care (EDQM) (2010): Filgrastim concentrated solution. European Pharmacopoeia 7.0, 2015-2018). For basic techniques the monograph cross-references to other chapters within the European Pharmacopoeia. These specifically referred chapters, which provide a more detailed description of the techniques, are cited in square brackets in the examples below. The utilised reference standards were either commercially purchased authorised drug products (filgrastim), approved by the European Union for medicinal use, or in-house standards which were calibrated using these commercial references. For the analysis of the relative potency in terms of International Units (IU) the International G-CSF Standard of the World Health Organisation (WHO) was used additionally. The test methods used for analysing the purity, the specific impurities, the G-CSF-related proteins and the biological activity (potency) were applied according the Ph. Eur. Monograph with few modifications only. Therefore, in the following, these standard analytical methods, which are known in the art, are described only briefly.

Example 13.1

Polyacrylamide Gel Electrophoresis (SDS-PAGE)

[Ph. Eur. 7, 2.2.31]. SDS-PAGE was used to determine the molecular size, the identity of G-CSF and the purity. The gels had 12% PA and include sodium dodecylsulfate (SDS). The method was used under reducing and non-reducing conditions. Gels were stained with Sypro ruby. To calculate the relative molecular masses (Mr) a panel of marker proteins with defined masses was used.

Example 13.2

High Performance Size-Exclusion Chromatography (SEC-HPLC): [Ph. Eur. 7, 2.2.30]. SEC was used to detect impurities or G-CSF-related substances with molecular masses higher than that of Filgrastim (dimers, aggregates). The detection of the proteins was based on UV absorption. The purity (main peak) and the impurities (dimers, aggregates) were expressed in area % of active substance for each component. The test results were calculated from the average of replicate measurements. FIG. 2 shows an example of a SEC chromatogram of a purified G-CSF batch (3B) in comparison with the reference standard (3A). Traces of aggregates are visible left from the main peak. The peak right from the main peak is caused by the solvent and not an impurity.

Example 13.3

Reversed Phase High Pressure Liquid Chromatography (RP-HPLC)

[Ph. Eur. 7, 2.2.9]. RP-HPLC was utilised to determine the identity of G-CSF, to calculate the G-CSF content and the purity. The method was also used to identify and quantify product-related substances. The detection of the proteins was based on UV absorption. The related protein impurities were expressed in percentage of active substance (% area). The test results were calculated from the average of replicate measurements.

Example 13.4

Isoelectric Focusing Gel Electrophoresis (IEF)

[Ph. Eur. , 2.2.54]. This method was used to detect impurities or product-related substances with charges differing from G-CSF (e.g. deamidated G-CSF). Separation was carried out in polyacrylamide gels containing immobilised pH gradients based on ampholytes. Additionally the isoelectric point (pI) of each protein band was calculated using a set of marker proteins having defined pIs.

Example 13.5

Enzyme-linked Immunosorbent Assay (ELISA)

This method was used for quantitative determination of E. coli host cell protein (HCP) levels. The test was performed by using a commercially purchased (generic) immunoenzymetric assay kit (Cygnus Technologies, no. F410). The solid phase of microtiter strips were coated with affinity-purified polyclonal anti-E. coli antibodies which captured HOP from the test samples. A tracer anti-E. coli antibody labeled with horseradish peroxidase (HRP) simultaneously bound to HOP and the resulting sandwich withstood washing procedures. Bound HCP, respectively HRP, was detected by oxidation of the substrate tetramethylbenzidine (TMB) in presence of hydrogen peroxide. The optical density was measured by an ELISA reader. Quantitation was performed with a calibration graph obtained by measuring HOP calibrators (provided by the kit) in different concentrations. The method was exactly performed according to the instructions of the supplier. HCP concentrations were expressed in ng/ml or ng/mg (ppm).

Example 13.6

Quantitative Polymerase Chain Reaction (gPCR)

This assay is used for the determination of E. coli host cell DNA. A commercially available kit was applied designated "resDNASEQ™ E. coli Residual DNA Quantitation System" which is based on the real-time TaqMan® qPCR technology (Applied Biosystems). The method is very sensitive and specific in detection of DNA contamination. The assay is based on sequence-specific amplification and real-time fluorescence detection of well defined DNA fragments by polymerase chain reaction (PCR) using sequence-specific primers (SSP) and fluorescently labeled hybridization probes (TaqMan®). The whole method including instrumentation, reagents, sampling and software-based calculation was performed according to the instructions of the supplier.

Example 13.7

Bacterial Endotoxins

[Ph. Eur. 7, 2.6.14, method C]. The detection of gram-negative bacterial endotoxins are globally harmonized standard methods based on amoebocyte lysates from horseshoe crab (*Limulus polyphemus*). This *Limulus* test ("LAL test") was carried out using the turbidimetric kinetic technique (method C) according to the European Pharmacopoeia. The results were expressed in International Units (IU) related to the International Endotoxin Standard BRP.

Example 13.8

Assay for Biological Activity (Relative Potency)

The biological activity of G-CSF samples was tested in a cell-based in-vitro proliferation assay as described in the filgrastim monograph with the following modifications. The bioassay method was based on the comparison of the change of the cell proliferation of NFS-60 cells, which originated from a murine myeloblastic cell line. NFS-60 cells were treated with dilution series of the test sample and the reference solution in parallel. The proliferation of the NFS-60 cells can be significantly and specifically stimulated with G-CSF. Propagation of the cells was performed in microtest plates for 72 hours. The proliferative effect was detected by using the substrate resazurin (alamar®Blue) which was converted by viable cells into the fluorescence dye resorufin. The fluorescence signal was detectable with high sensitivity. The parallel line assay calculation of the dose response curves, with at least three points in the linear part of the curves, was used as a statistical evaluation. Acceptance range was between 80% and 125% compared to the reference solution. The relative potency was expressed by International Units (IU) which were defined by internal standards calibrated to the International WHO standard for filgrastim. Fully active, pure human G-CSF possesses a specific biological activity of $1.0 \times 10^8$ IU/mg.

Example 13.9

Peptide Mapping

[Ph. Eur. 7, 2.2.55]. The peptide mapping followed by mass spectroscopy (MS) analysis was used for analysis of the disulfide-bridges. The enzymatic cleavage of the peptide bonds procedure was developed on the basis of the Ph. Eur. monograph for filgrastim. The protease used for cleavage was Glutamyl Endopeptidase (EndoGlu-C). Incubation was carried out at 37° C. for 24 hours and stopped by addition of 8M GuHCl and boiling. The peptide mapping procedure was performed under reduced and non-reduced conditions. The resulting differences in the MS spectrum of the peptide profiles for reduced and non-reduced conditions prove the position of the disulfide bonds. Completely folded intact G-CSF (filgrastim) has two disulfide bridges at positions Cys37-Cys43 and Cys65-Cys75, while one cysteine residue is free at position 18.

Alternatively peptides obtained from G-CSF samples after the proteolytic digestion can be separated in a RP-HPLC system and detected in UV. This method provides comparative data, as the fingerprint-like chromatogram obtained with the test solution is compared to the chromatogram obtained with the reference material.

List of References
1. R. R. Burgess, 1996 "Purification of over produced E. coli RNA polymerase σ factors by solubilizing inclusion bodies and refolding from sarkosyl". Methods Enzymol. 273, 145-149
2. David C. Dale, 2002, "Colony-Stimulating Factors for the Management of Neutropenia in Cancer Patients", Aids International Limited Drugs 2002; 62 Suppl. 1, 1-15
3. P. E. Devlin, 1988, "Alteration of amino-terminal codons of human granulocyte-colony-stimulating factor increases expression levels and allows processing by methionine aminopeptidase in Escherichia coli", Elsevier Science Publishers B.V. (Biomedical Division) Gene, 65, 13-22
4. Arndt Dietrich et al., Jan 2003 "Industrial Protein Folding", www.gitverlag.com/go/bioint BIO forum Europe, 1-3
5. European Pharmacopoeia, Jul 2010 "Filgrastim concentrated solution"; 2015-2018
6. Elanders Ö stervala, April 2007 "Purification and renaturation of recombinant proteins produced in Escherichia coli as inclusion bodies, www.gelifesciences.com/protein-purifactoin Application note 18-1112-33 AC, 1-4
7. Glover, D. M. DNA Cloning Volume I: A Practical Approach. IRL Press, Oxford, 1985.
8. M. Heidari et al., May 2001, "Expression, purification, and in vitro biological activities of recombinant bovine granulocyte-colony stimulating factor", www.elsevier.com/locate/vetimm Veterinary Immunology and Immunopathology 81, 45-57
9. Holloway C. J, 1994, "Applications of Recombinant DNA Technology in the Production of Glycosylated Recombinant Human Granulocyte Colony Stimulating Factor", European Journal of Cancer Vol. 30 A, Suppl. 3, S2-S6
10. Soo-Hyung Kang et al., July 1995, "High Level Expression and Simple Purification of Recombinant Human Granulocyte Colony-Stimulating Factor in E. coli, Biotechnology Letters Volume 17 No. 7 687-692
11. Khalilzadeh R. et al., July 2008, "Process development for production of human granulocyte-colony stimulating factor by high cell density cultivation of recombinant Escherichia coli, J. Ind Microbiol Biotechnol, 1643-1650
12. Fiona A. O. Marston, 1986, "The purification of eukaryotic polypeptides synthesized in Escherichia coli, Biochem. J. (1986) Vol. 240, 1-12
13 G. Molineux, 2004, "The Design and Development of Pegfilgrastim", Current Pharmaceutical Design, 2004, 10, 1235-1244
14. Dasari Venkata Krishna Rao et al., 2008, "A purification method for improving the process yield and quality of recombinant human granulocyte colony-stimulating factor expressed in Escherichia coli and ist characterization, Biotechnol. Appl. Biochem. (2008) 50, 77-87
15. Harald Tschesche, 1990, "Modern Methods in Protein- and Nucleic Acid Research", Walter de Gruyter, Berlin, NY, 149-171
16. Rainer Rudolph et al., January 1996, "In vitro folding on inclusion body proteins", The FASEB Journal Vol. 10, 49-56
17. Sambrook, J., Fritsch, E. F., and Maniatis, T., in Molecular Cloning: A Laboratory Manual. Cold Spring Harbor Laboratory Press, NY, Vol. 1, 2, 3 (1989)
18. Ana L S Vanz et al., April 2008, "Human granulocyte colony stimulating factor 8hG-CSF): cloning, overexpression, purification and characterization", Microbial Cell Factories 2008, www.micorbialcellfactories.com/content/7/1/13, 1-12
19. Chao Zan WANG et al., 2005, "Refolding with Simultaneous Purification of Recombinant Human Granulocyte Colony-stimulating Factor from Escherichia coli, Chinese Chemical Letters Vol. 16 No. 3 www.imm.ac.cn/journal/ccl.html, 389-392
20. Karl Welte et al., September 1996, "blood", Blood Vol. No. 8, American Society of Hematology www.bloodjournal.org, 1907-1929
21. Paul WINGFIELD et al., 1988, "Characterization of recombinant-derived granulocyte-colony stimulating factor (G-CSF)", Biochem. J. Vol. 256, 213-218
22. Krisztina M. Zsebo et al., 1986, "Recombinant Human Granulocyte Colony Stimulating Factor: Molecular and Biological Characterization, Immunobiol., Vol. 173, 175-184
23. Lu et al, 1992, The Journal of biological Chemistry, Vol 267:8770-8777
24. WO 03/051922 A1
25. WO 01/87925 A2
26. WO 01/04154 A1
276. WO 00/02901
28. U.S. Pat. No. 6,489,450 B2
29. U.S. Pat. No. 5,849,883
30. U.S. Pat. No. 5,681,720
29. U.S. Pat. No. 5,055,555
31. EP 1 837 346 A2
32. EP 1 630 173 A2
33. EP 0 219 874 A2
34. WO 2010/146599 A1
35. WO 2008/096370 A3
36. WO 2006/135176 A1
37. WO 2006/097944 A2
38. WO 2004/015124 A1
39. WO 2004/001056 A1
40. WO 98/53072
41. WO 89/10932
42. WO 87/01132

The invention claimed is:

1. A method for the production of a recombinant polypeptide in inclusion bodies, the method comprising
   (a) cultivating a bacterial host cell at a first temperature, the host cell comprising a nucleic acid encoding said recombinant polypeptide,
   (b) lowering the cultivation temperature from the first temperature to a second temperature, and
   (c) cultivating the bacterial host cell at the second temperature,
wherein lowering of the temperature is performed when the cell culture has reached an optical density at 600 nm of between 10 and 50.

2. The method of claim 1, wherein the bacterial host cell is *E. coli*.

3. The method of claim 1, wherein the first temperature is between 36° C. and 38° C.

4. The method of claim 3, wherein the first temperature is 37° C.

5. The method of claim 1, wherein the second temperature is between 25° C. and 36° C.

6. The method of claim 5, wherein the second temperature is between 30° C. and 36° C., between 30° C. and 35° C., or between 31° C. and 33° C.

7. The method of claim 1, wherein the pH during cultivation at the first temperature and/or the second temperature is between 6 and 8.

8. The method of claim 7, wherein the pH during cultivation at the first temperature and/or the second temperature is between 6.8 and 7.2.

9. The method of claim 1, wherein the nucleic acid is operably linked to an inducible promoter.

10. The method of claim 1, wherein lowering of the temperature is performed when the cell culture has reached an optical density at 600 nm of between 27 and 33.

11. The method of claim 1, wherein the recombinant polypeptide is a four-helix-bundle polypeptide.

12. The method of claim 1, wherein the recombinant polypeptide is G-CSF.

13. The method of claim 12, wherein the recombinant polypeptide is G-CSF and wherein the G-CSF is human or bovine G-CSF.

14. The method of claim 13, wherein the G-CSF is human or bovine G-CSF, with an initial methionine amino residue at position 1, respectively.

15. The method of claim 1, further comprising a step, preceding step (a), of introducing into a host cell an expression vector comprising a nucleic acid encoding said recombinant polypeptide, wherein the nucleic acid is operably linked to an inducible promoter.

16. The method of claim 9, wherein the inducible promoter is a T7 promoter.

17. The method of claim 1, wherein the chromosome of the bacterial host cell comprises a nucleic acid sequence coding for a bacteriophage RNA polymerase, and is free of lysogenic bacteriophage nucleic acid sequences.

18. The method of claim 17, wherein the nucleic acid sequence is operably linked to a lac promoter.

19. The method of claim 17, wherein the bacteriophage RNA polymerase is T7 polymerase.

20. The method of claim 1, wherein expression of the polypeptide is performed by addition of an inducer.

21. The method of claim 20, wherein the inducer is added simultaneously with or subsequently to lowering the temperature.

22. The method of claim 20, wherein the inducer is IPTG.

23. The method of claim 15, wherein the vector comprises the sequence of SEQ ID NO:4.

24. The method of claim 1, wherein the nucleic acid encoding said recombinant polypeptide is selected from the group consisting of
   (i) a nucleic acid sequence encoding the polypeptide of SEQ ID NO:3 or SEQ ID NO:1; and
   (ii) a nucleic acid sequence encoding a polypeptide having a sequence identity of at least 90% to the sequence as depicted in SEQ ID NO:3.

* * * * *